US010403399B2

(12) United States Patent
Shah

(10) Patent No.: US 10,403,399 B2
(45) Date of Patent: Sep. 3, 2019

(54) TASKS SCHEDULING BASED ON TRIGGERING EVENT AND WORK LISTS MANAGEMENT

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 879 days.

(21) Appl. No.: 14/946,702

(22) Filed: Nov. 19, 2015

(65) Prior Publication Data

US 2016/0147955 A1    May 26, 2016

Related U.S. Application Data

(60) Provisional application No. 62/082,263, filed on Nov. 20, 2014.

(51) Int. Cl.
*G06F 19/00* (2018.01)
*G16H 40/20* (2018.01)
*G06Q 10/06* (2012.01)
*G16H 40/63* (2018.01)
*G16H 10/65* (2018.01)

(52) U.S. Cl.
CPC ....... *G16H 40/20* (2018.01); *G06Q 10/06311* (2013.01); *G16H 10/65* (2018.01); *G16H 40/63* (2018.01)

(58) Field of Classification Search
None
See application file for complete search history.

(56) References Cited

U.S. PATENT DOCUMENTS

| 7,310,607 | B2 | 12/2007 | Brandt et al. |
| 7,796,045 | B2 | 9/2010 | Spear et al. |
| 8,571,907 | B2 | 10/2013 | Jones, Jr. |
| 9,600,633 | B2 | 3/2017 | Coffman et al. |
| 10,062,457 | B2 | 8/2018 | Garibaldi |
| 10,064,579 | B2 | 9/2018 | Condurso et al. |
| 2003/0149598 | A1* | 8/2003 | Santoso ......... G06Q 10/063112 705/2 |
| 2006/0053035 | A1* | 3/2006 | Eisenberg ............. G16H 40/20 705/2 |

(Continued)

*Primary Examiner* — Michael Tomaszewski
(74) *Attorney, Agent, or Firm* — Rahman LLC

(57) ABSTRACT

A computer-implemented method for scheduling, tracking, and executing performance of a set of tasks includes defining a time series, associating a current time occurrence on the time series, and associating a future time occurrence on the time series. The method includes creating a tasks list including the set of tasks. The method includes defining an interaction zone rule in association with the time series and triggering events to initiate the set of tasks. The method includes scheduling a task from the set of tasks at the future time occurrence relative to the current time occurrence based on occurrence of a triggering event in view of the interaction zone rule. The method includes receiving an output from an event monitor at a control server. The method includes notifying a remote device for performance of the scheduled task at the future time occurrence upon detection of the triggering event.

20 Claims, 18 Drawing Sheets

(56) References Cited

U.S. PATENT DOCUMENTS

| | | | |
|---|---|---|---|
| 2007/0129983 A1* | 6/2007 | Scherpbier | G06Q 50/22 705/2 |
| 2008/0164998 A1 | 7/2008 | Scherpbier et al. | |
| 2009/0112618 A1 | 4/2009 | Johnson et al. | |
| 2009/0313046 A1* | 12/2009 | Badgett | G06Q 10/06 705/3 |
| 2010/0094656 A1 | 4/2010 | Conant | |
| 2011/0106565 A1 | 5/2011 | Compton et al. | |
| 2011/0184250 A1 | 7/2011 | Schmidt et al. | |
| 2013/0103412 A1* | 4/2013 | Nudd | G06Q 10/1097 705/2 |
| 2013/0191145 A1* | 7/2013 | Nudd | G06Q 10/063118 705/2 |
| 2015/0040134 A1 | 2/2015 | Leggette et al. | |
| 2015/0066529 A1* | 3/2015 | Lattuca | G06Q 50/22 705/2 |
| 2015/0154528 A1* | 6/2015 | Kharraz Tavakol | G06Q 10/0631 705/2 |

\* cited by examiner

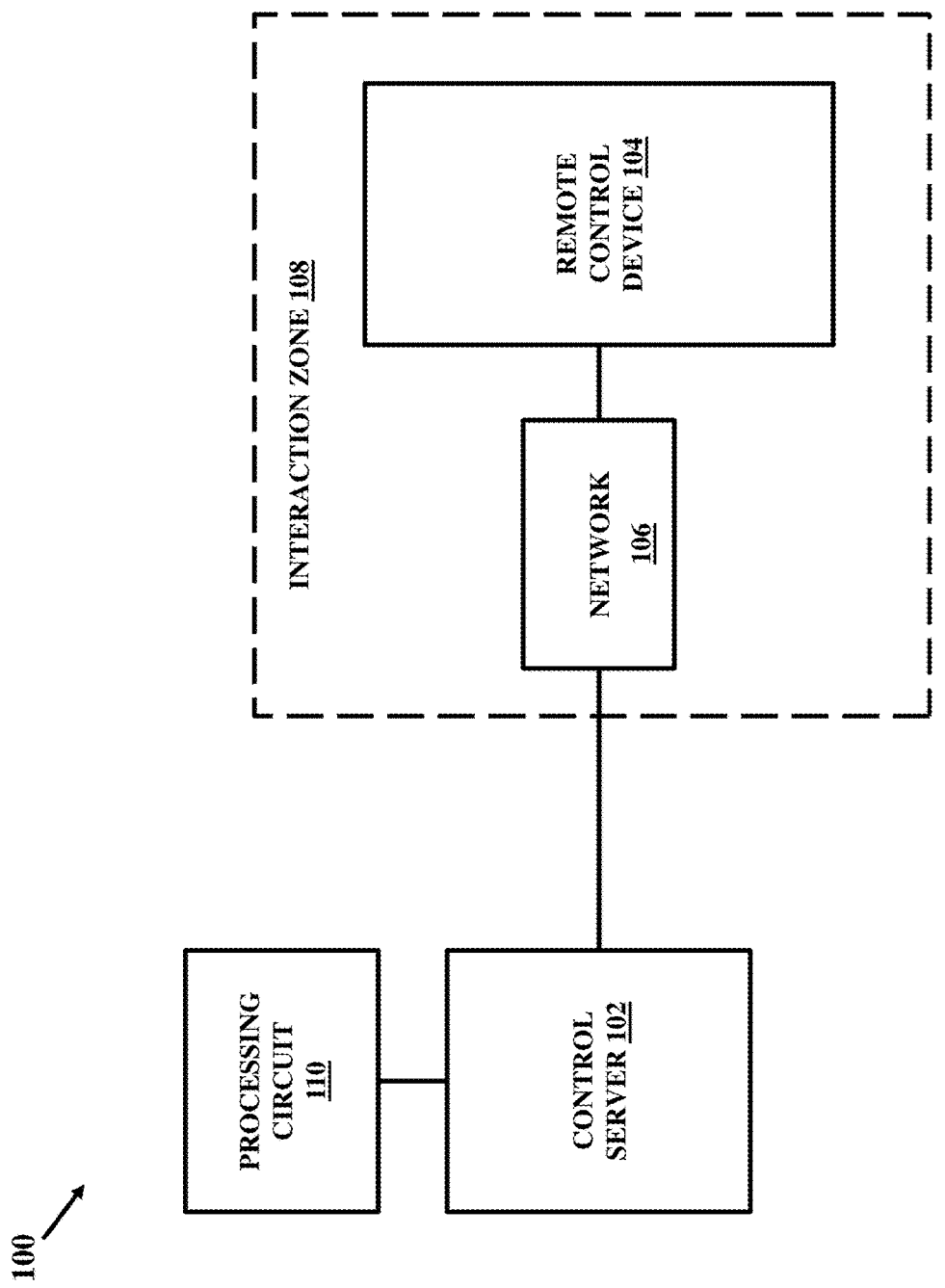

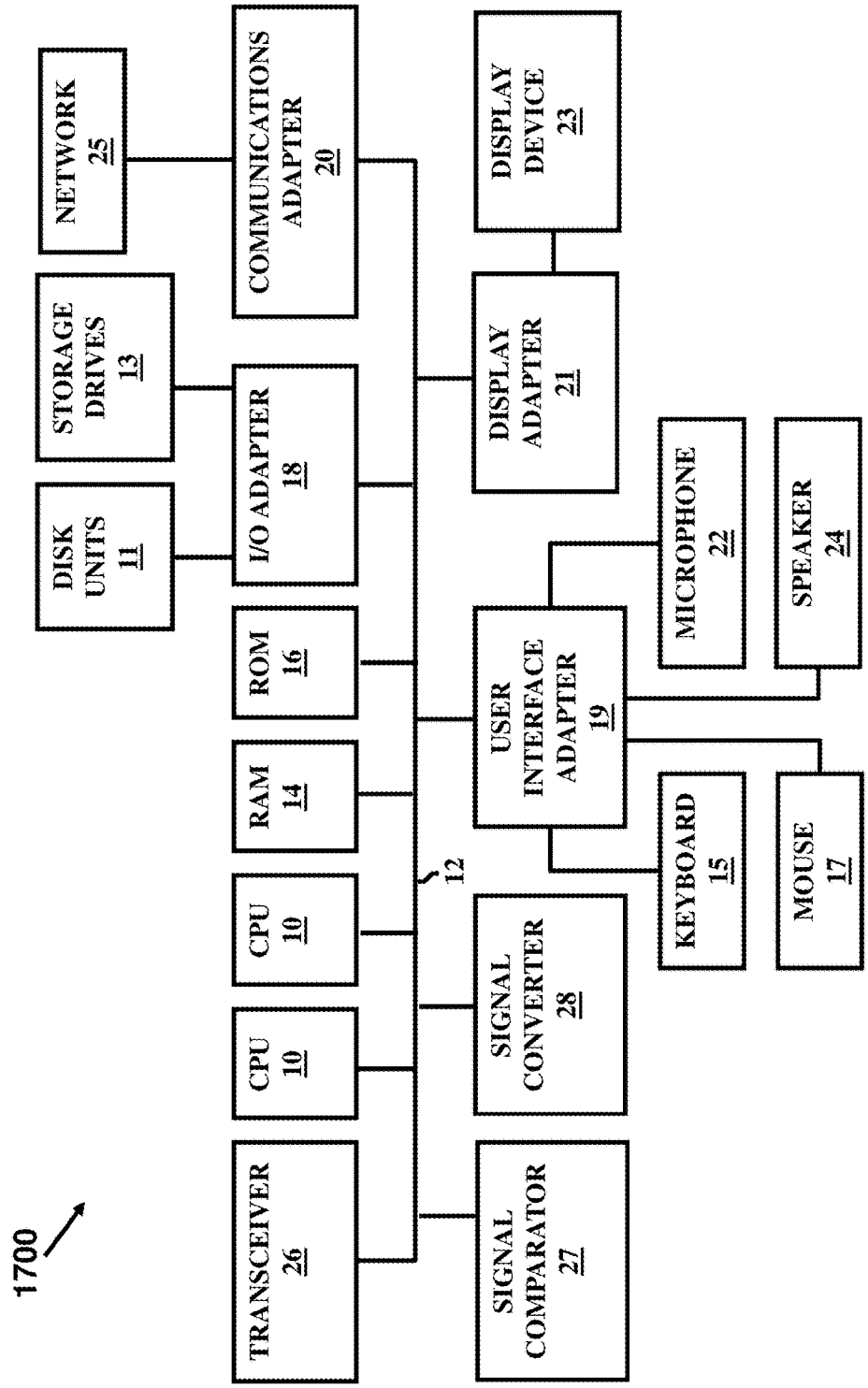

TASKS SCHEDULING BASED ON TRIGGERING EVENT AND WORK LISTS MANAGEMENT

CROSS-REFERENCE TO RELATED APPLICATIONS

This application claims the benefit of U.S. Provisional Application No. 62/082,263, filed on Nov. 20, 2014 and entitled "Tasks Scheduling Based on Triggering Event and Work Lists Management," the complete disclosure of which, in its entirety, is hereby incorporated by reference.

BACKGROUND

Technical Field

The embodiments herein generally relate to tasks management, and more particularly to methods and systems for scheduling and execution of predefined tasks.

Description of the Related Art

Healthcare providers visit for example elderly patients for routine checkup, glucose monitoring, blood analysis, blood pressure check and other similar tasks. In some cases, healthcare providers need something from patients regularly but do not necessarily want a special trip by the healthcare providers to visit the patients every time. However, the current methods and systems do not allow healthcare providers to take care of these issues without having them to visit the patients every time.

In view of the above, there is a need for an improved method and system for allowing healthcare providers to establish rules based on defined parameters to drive certain actions associated with patients.

SUMMARY

An embodiment herein provides a computer-implemented method for scheduling, tracking, and executing performance of a set of tasks. The method includes defining, by a special purpose processor in a repository, a time series, associating, by the special purpose processor in the repository, a current time occurrence on the time series, and associating a future time occurrence, by the special purpose processor in a repository, on the time series, wherein the future time occurrence is defined as a succeeding time occurrence on the time series in relation to the current time occurrence. The method further includes creating a tasks list including the set of tasks by a processing circuit, wherein the tasks list includes an actionable questionnaire, a test plan, a process verifier, a runbook, a careplan, a regulatory mandate that each are editable and executable at the future time occurrence. The method may further include defining an interaction zone rule in association with the time series, wherein the step of defining the interaction zone rule includes defining a plurality of triggering events, by the special purpose processor, to initiate the set of tasks. The method may include associating the interaction zone rule with one or more participants in the repository and scheduling a task from the set of tasks at the future time occurrence relative to the current time occurrence based on occurrence of a triggering event in view of the interaction zone rule. The method may include receiving an output from an event monitor at a control server. The output is indicative of the triggering event at the future time occurrence. The method may include notifying the remote device for performance of the scheduled task at the future time occurrence upon detection of the triggering event. The step of notifying may include generating an electric signal comprising data signifying the schedule task and instructions for performance of the scheduled task, transmitting the electric signal from the control server, communicatively connected with the special purpose processor, in a network comprising a plurality of communicatively linked data communication devices, converting the electric signal into a plurality of pixels, and displaying the plurality of pixels on a display unit of the remote device to launch an activation message that includes an instruction to perform the scheduled task at the future time occurrence upon occurrence of the triggering event in accordance with the interaction zone rule. The method further includes receiving a message by the control server from the remote device to update the set of tasks list and the time series dynamically based on a performance status of the scheduled task and replacing the future time occurrence with a new current time occurrence in the repository and defining a new future time occurrence on the time series based on the performance status of the scheduled task and an input from the remote device that is indicative of health of a patient.

An embodiment herein provides a computer-controlled system for scheduling, tracking, and executing performance of a set of tasks. The system includes a control server configured to communicatively connect with a remote device through a network for allowing exchange of computer executable patient data between the control server and the remote device. The system further includes a special purpose processor included within or communicatively connected with the control server to define a time series in a repository, associate a current time occurrence on the time series in a repository, associate a future time occurrence on the time series in a repository, wherein the future time occurrence is defined as a succeeding time occurrence on the time series in relation to the current time occurrence, create a tasks list including the set of tasks in a repository, wherein the tasks list includes an actionable questionnaire, a test plan, a process verifier, a runbook, a careplan, a regulatory mandate that each are editable and executable at the future time occurrence, define an interaction zone rule in association with the time series. The step of defining the interaction zone rule includes defining a plurality of triggering events, by the special purpose processor, to initiate the set of tasks, associate the interaction zone rule with one or more participants in a repository, schedule a task from the set of tasks at the future time occurrence relative to the current time occurrence based on occurrence of a triggering event in view of the interaction zone rule, receive an input indicative of the triggering event at the future time occurrence, and notify the remote device for performance of the scheduled task at the future time occurrence upon detection of the triggering event. The step of notifying includes generating an electric signal comprising data signifying the schedule task and instructions for performance of the scheduled task, transmitting the electric signal in a network comprising a plurality of communicatively linked data communication devices, converting the electric signal into a plurality of pixels, displaying the plurality of pixels on a display unit of the remote device to launch an activation message that includes an instruction to perform the scheduled task at the future time occurrence upon occurrence of the triggering event in accordance with the interaction zone rule, receive a message from the remote device to update the set of tasks list and the time series dynamically based on performance status of the task, replace the future time occurrence with a new current time occurrence and define a new future time occurrence on the time series in a repository based on the performance status of the scheduled task and an input from the remote device that is indicative of health of a patient. The system further includes an event monitor comprising a location sensor and a weather sensor communicatively connected with the control server for detecting spatial presence and a weather controlled event respectively upon occurrence of the triggering event.

An embodiment herein provides a computer-controlled worklists management system for creating, scheduling and facilitating execution of a computer executable worklist across a plurality of distributed execution servers. The system includes a processing circuit to generate the computer executable worklist. The computer executable worklist includes a plurality of tasks scheduled to be executed at a future time occurrence on a time series based on occurrence of a triggering event in view of an interaction zone rule indicative of a spatial presence and a weather controlled event within an interaction zone, wherein the plurality of tasks include at least a first task executable by a first device controlled by a first execution server, a second task executable by a second device controlled by a second execution server, a third task executable by a third device controlled by a third execution server. The first execution server, the second execution server, and the third execution server are located remotely in a distributed environment. The system further includes a worklists storage repository. The worklists storage repository includes a worklists library containing predefined and user editable worklist templates. The worklists library includes a survey template, a check list template, a care plan template, a questionnaire template, and a protocol template. The worklists storage repository includes a task library containing user generated and user editable tasks such that the tasks are editable using predefined control options, wherein the tasks are configured to be imported in a select worklist template from among the worklist templates to generate the computer executable worklist. The system further includes a memory circuit coupled to the processing circuit and storing a plurality of application programming interfaces (APIs) providing a stack of API layers including a system API layer to allow communication with 1) customer applications with API capability directly 2) customer applications without API capability indirectly, wherein the customer applications reside at the first device, the second device, and the third device, a supplementary modular, reusable and variably configurable independent API layer for secure authentication, data transfer, and data handling applications configured for interaction zone parameters signifying the triggering event comprising the spatial presence and weather-controlled event, a business process modeling layer that unifies the worklists storage repository with the processing circuit, and a data abstraction layer for enabling communication between the processing circuit and various data stores. The system further includes a file-based interaction device including a first component communicatively and operatively connected with the processing circuit and a second component communicatively and operatively coupled with the first device, the second device, and the third device, wherein the second component comprises an installable agent to: cause the customer applications without API capability to interact with the system APIs indirectly through the first component and the second component, to collect information from the first device, the second device and the third device, and to interact with the workflow storage engine.

BRIEF DESCRIPTION OF THE DRAWINGS

In the drawings, like numerals describe similar components substantially throughout the several views. The drawings illustrate generally, by way of an example, but not by a way of limitation, various embodiments.

FIG. 1A illustrates an exemplary architecture for managing healthcare functions in accordance with an embodiment herein;

FIG. 17 illustrates a computer system used in accordance with the embodiments herein.

DETAILED DESCRIPTION

Figure 1B:
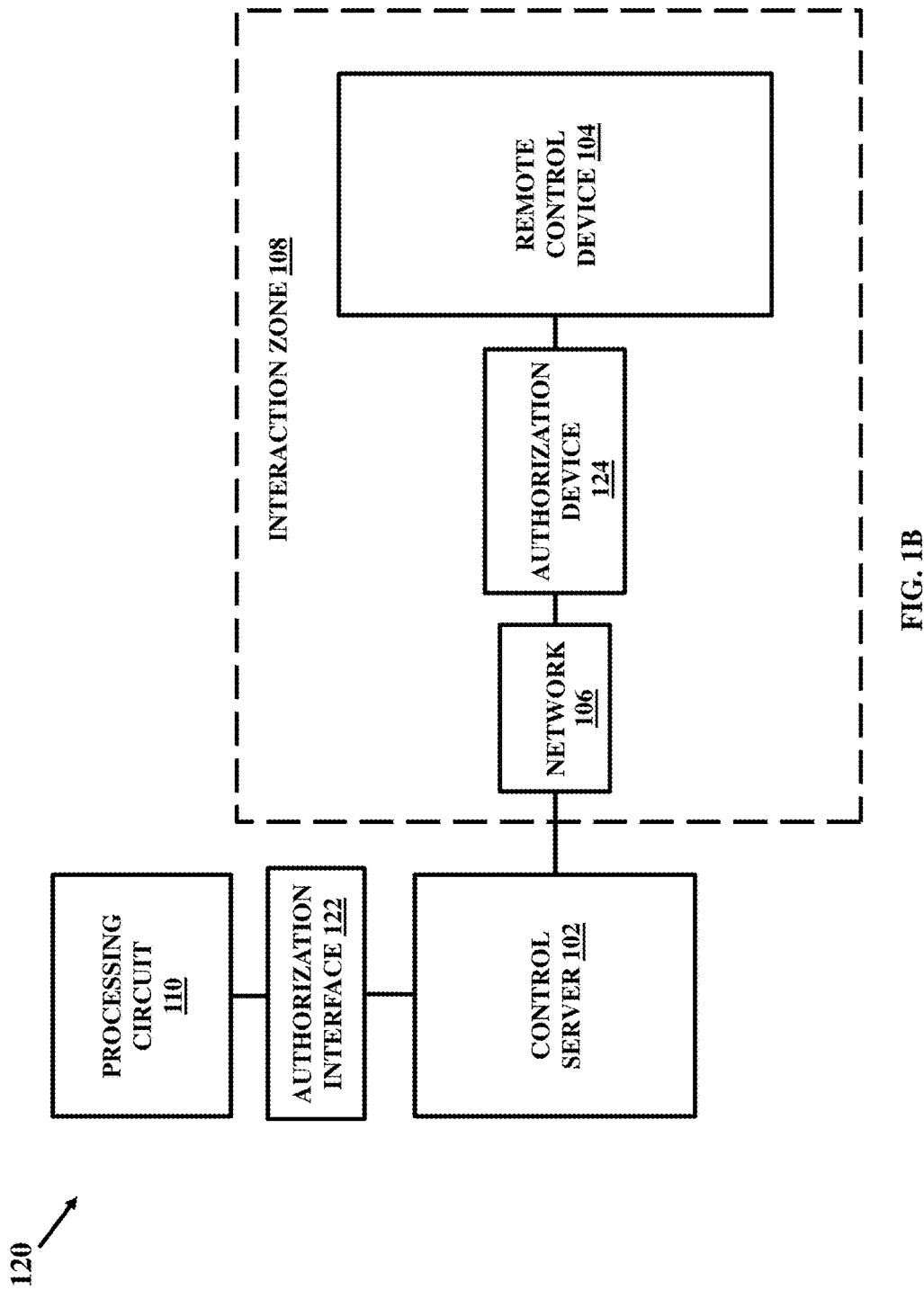
FIG. 1B illustrates an exemplary architecture for managing healthcare functions in accordance with an embodiment herein.

In the following detailed description, reference is made to the accompanying drawings that form a part hereof, and these are shown by way of illustrating specific embodiments herein that may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

In this document, the terms "a" or "an" are used, as is common in patent documents, to include one or more than one. In this document, the term "or" is used to refer to a "nonexclusive or" unless otherwise indicated.

FIG. 1A illustrates an exemplary architecture 100 for managing healthcare functions in accordance with an embodiment herein. The architecture 100 may include a control server 102 communicatively connected with a remote control device 104 over a network 106 when the remote control device 104 is in the proximity of or within an interaction zone 108. The interaction zone 108 may be a physical space with defined technical capabilities such as a hospital, a nursing center, home of a patient or any other location where a patient may be situated and that may possess capabilities of receiving and/or sending computer executable instructions from/to the control server 102.

In accordance with the illustrated embodiment, the control server 102 is remotely located from the interaction zone 108. In other embodiments, the control server 102 may be configured within the interaction zone 108. The interaction zone 108 provides a dedicated facility for controlled and secured healthcare information storage, exchange and solutions delivery. For example, the interaction zone 108 may be enabled to be networked through the network 106 so as to allow communication between the control server 102 and the remote control device 104 whenever the remote control device 104 is in the proximity of the interaction zone 108. The remote control device 104 may be a handheld device, a patient monitoring device, a mobile device, or a mobile phone, or a customized remote device with pre-launched application layers for executing a set of applications enabling communication of the computer executable instructions across the network 106, and the like. The remote control device 104 may be configured to receive computer executable instructions from the control server 102 and allow information exchange between the control server 102, the remote control device 104, and other similar remote control devices operating within the interaction zone 108 or in association with a patient within the interaction zone 108.

The control server 102 is communicatively coupled with a processing circuit 110 for executing computer readable instructions stored within the control server 102 or received from the control server 102 for allowing performing a set of tasks by a practitioner by communicating a message to the remote control device 104 through the network 106.

In embodiments, the remote control device 104 may include such as a user computer or any other computing device or handheld device that includes input devices (such as a keyboard, mouse, microphone, etc.) and output devices (such as a monitor, printer, or speaker, etc.). The remote client device 104 may also include network connections to other devices, computers, networks, servers, etc., that are connected to the network 106. In some embodiments, the network 106 is a local area network (LAN), a wide area network (WAN), an intranet or extranet, or a combination thereof. Communications with the network are implemented using wired and/or wireless technologies. Other configurations may be possible.

In some examples, the practitioner may include such as a doctor, physician, or other persons or groups or institutions, other healthcare providers, other service providers or other types of professionals, or group of professionals or institutes etc who may be authorized to perform the set of tasks on patients or other relevant persons within the interaction zone 108.

The remote control device 104 may communicate with the processing circuit 110 and the control server 102 through the network 106.

FIG. 1B, with reference to FIG. 1A, illustrates an exemplary architecture 120 for authorizing the user and managing healthcare functions in accordance with an embodiment herein.

In an embodiment, an authorization interface 122 receives input from the user for authorizing the user to access the interaction zone 108 or the remote control device 104. In an embodiment, the authorization interface 122 may be a specific device connected to the processing unit 122 or the control server 102. In an embodiment, the authorization interface 110 is integrated with the processing circuit 110. In an embodiment, the authorization interface 122 is included in or integrated with the control server 102.

In an embodiment, authorization interface 122 is configured to implement one or a plurality of user authorization or authentication policies. User authorization policy may include manual input of credentials by the user. In an embodiment, user authorization policy may include reading an identification card by the authorization interface 122. The identification card may be a unique card issued to the user, or a card with specific credentials unique to the user.

In an embodiment an authorization device 124 is configured to authenticate the communication received from the user. In an embodiment, the authorization device may be a specific device connected to network 106 and the remote control device 104. In an embodiment, the authorization device 124 may be integrated in network 106, or integrated in the remote control device 104.

The authorization device 124 may be configured to use the authorization policy implemented by the authorization interface 122. For example the authorization device 122 may be configured to verify the credentials manually entered by the user, or be configured to verify the information generated through using the identification card of the user.

Figure 2:
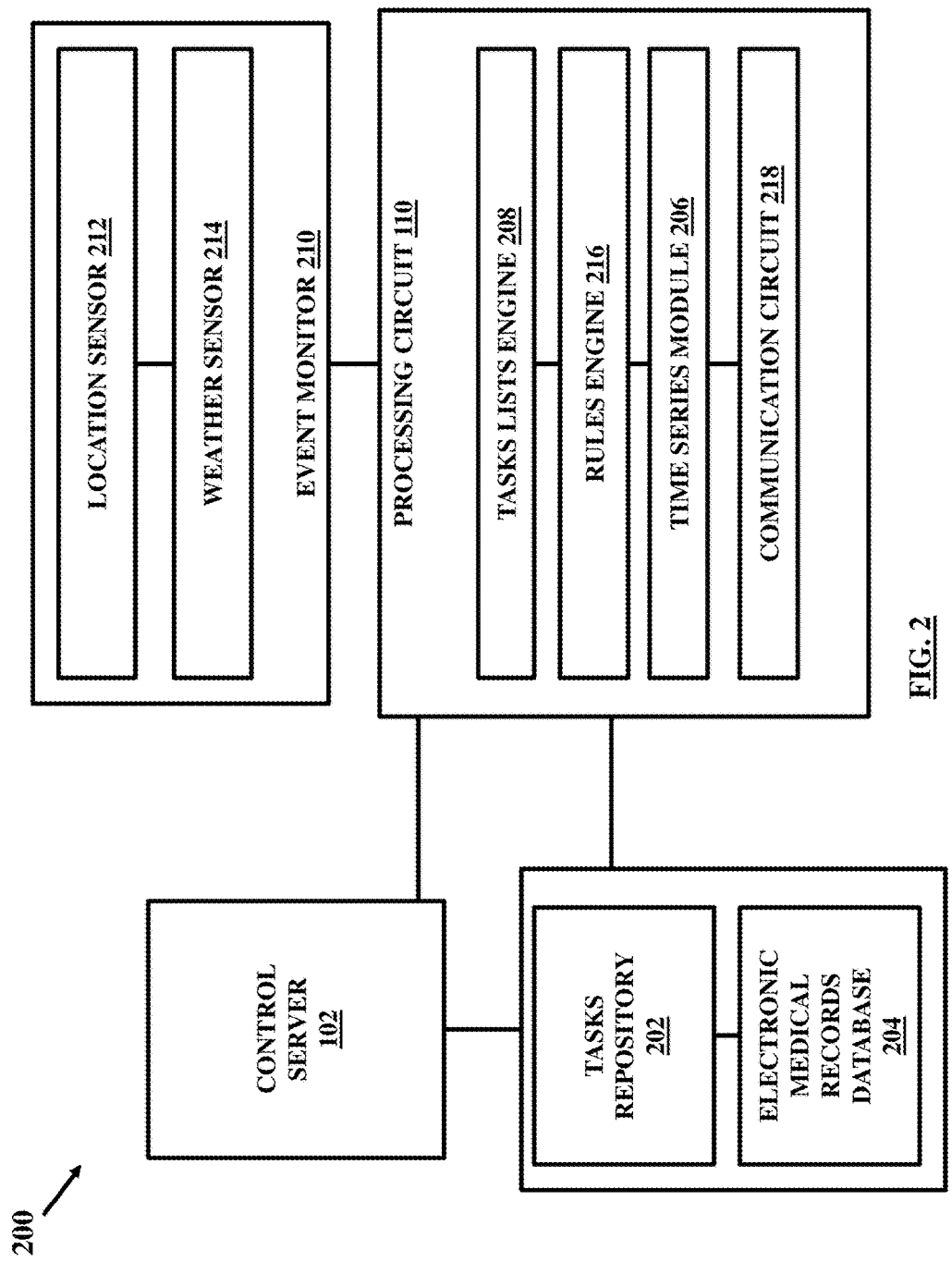
FIG. 2 illustrates a detailed block diagram of a processing circuit among other things, in accordance with an embodiment herein.

FIG. 2, with reference to FIG. 1A through FIG. 1B, illustrates a detailed block diagram of the processing circuit 110 among other things, in accordance with an embodiment herein. The processing circuit 110 may be coupled to the control server 102, a tasks repository 202, and an electronic medical records database 204. The control server 102 may be further communicatively coupled with the tasks repository 202 and the electronic medical records database 204. The electronic medical records database 204 may store computer executable patient files or computer executable patient data. In an example, the electronic medical records database 204 may be a dedicated data center for retrieving and storing patient data through integrated devices associated with patients. In this case, the computer executable patient data may be device generated data obtained from the integrated devices over the network 106 in a secured manner. In an example, the electronic medical records database 204 may store computer executable patient medical files, computer executable patient historical records or prescriptions, and the like. Each computer executable electronic medical record or patient file is associated with a first identification code that is indicative of a patient's identity. Each computer executable electronic medical record is further associated with a second identification code that is indicative of a practitioner associated with the patient. Each computer executable electronic medical record is further associated with a third identification code that is indicative of a set of tasks recommended by the practitioner associated with the patient in a last visit for the patient so that the third identification code directly links the computer executable electronic medical records stored in the electronic medical records database 204 with the tasks repository 202 that stores the set of tasks associated or scheduled to be associated with the patient at a future time occurrence. The tasks repository 202 stores the set of tasks associated with the patient. The tasks repository 202 may be communicatively connected with an interface engine that provides a communication link between the tasks repository 202 and the electronic medical records database 204 so as to associate the set of tasks with the computer executable patient files for generating a user configurable updated set of tasks list when the practitioner or the remote control device 104 is within the interaction zone 108.

The processing circuit 110 includes a time series module 206 that executes computer readable instructions to define a time series and associate a current time occurrence and a future time occurrence on the time series. In an example, the future time occurrence is in relation to a successive time slot on the time series as compared to the current time occurrence. The current time occurrence is predefined and may be defined as a reference to the future time occurrence. In an example, the current time occurrence may be associated with a practitioner's current or last visit in the interaction 108 zone in association with the first identification, and/or second identification code and/or third identification code for performing certain tasks for the patient. In an example, the future time occurrence may be predefined based on the first identification code and/or second identification code, and or third identification and/or the set of tasks last performed. In an embodiment, the future time occurrence may not be predefined and the future time occurrence is associated to be defined in real time based on an occurrence of an event in future time that occurs at a successive slot in the time series in relation to the current time occurrence. The successive slot may be associated with a next event occurrence or after an event has occurred defined times such as two, three or four times.

The processing circuit 110 further includes a tasks list engine 208 that generates the set of tasks associated with the patient and associates the third identification code with the set of tasks list so generated by the tasks list engine 208.

The processing circuit 110 may be communicatively coupled to an event monitor 210 to detect or receive an input pertinent to the event or triggering event that triggers scheduling or performing of the set of tasks within the interaction zone 108. In an example, the triggering event may be a weather controlled event. In an embodiment, the triggering event may be a spatial presence that is indicative of a presence of the remote control device 104 associated with a practitioner with a defined identification code within the interaction zone 108 at the future time occurrence.

The event monitor 210 may include a location sensor 212 that detects the spatial presence of the remote control device 104 within the interaction zone 108. The location sensor 212 may include a GPS instrument or any other type of monitoring device. The event monitor 210 may further include a weather sensor 214 that monitors weather parameters or weather controlled triggering events such as humidity, rains, temperature, and the like.

In an embodiment, the processing circuit 110 may include a rules engine 216 that executes computer readable instructions for developing and/or executing a set of rules that cause the practitioner to perform a task from the set of tasks lists based on occurrence of a triggering event as identified from the received input from the event monitor 210 that may include one or a plurality of sensors, cameras, scanners and the like. The rules engine 216 may execute different tasks for different triggering events based on the input received from the event monitor 210. The rules engine 216 may execute the set of computer executable rules that are stored within the control server 102 or an external repository located within the interaction zone 108 or outside the interaction zone 108.

In an example, the event monitor 210 may be communicatively connected with the processing circuit 110 through data aggregators that may aggregate data from the various sensors contained within the event monitor 210. The data may be communicated to the processing circuit 110 through various gateways.

The processing circuit 110 launches an activation message when the input indicative of the triggering event is received. The message is sent to the remote control device 104 by a communication circuit 218 over the network 106 that is displayable over the remote control device 104 and is indicative to perform a task from the set of tasks by the practitioner associated with the remote control device 104 at the future time occurrence upon occurrence of the triggering event in accordance with the established rules. Once the task is performed by the practitioner at the future time occurrence, the remote control device 104 may send a message to the processing circuit 110 to update the set of tasks list and the time series automatically and dynamically based on performance status of the task by the practitioner. In case the task is successfully performed, the current time occurrence replaces the future time occurrence and a new future time occurrence is defined on the time series based on an input from the remote control device 104 that is indicative of a health status of the patient. For example, the time series may redefine and associate the future time occurrence for the next slot on the time series or next visit of the practitioner within the interaction zone 108 if the patient health status indicates a critical situation. On the contrary, if the patient recovery is expected to speed up, the future time occurrence may be associated after a certain number of slots on the time series such as after three visits of the practitioner and the like and not on the consecutive visits or consecutive weather controlled events and the like. The slots on the time series may represent different instances associated with the triggering events. For example, next visit instance of a practitioner with a defined identification code in the interaction zone 108 may be referred to as a next slot on the time series wherein the practitioner's visit is a triggering event.

Figure 3:
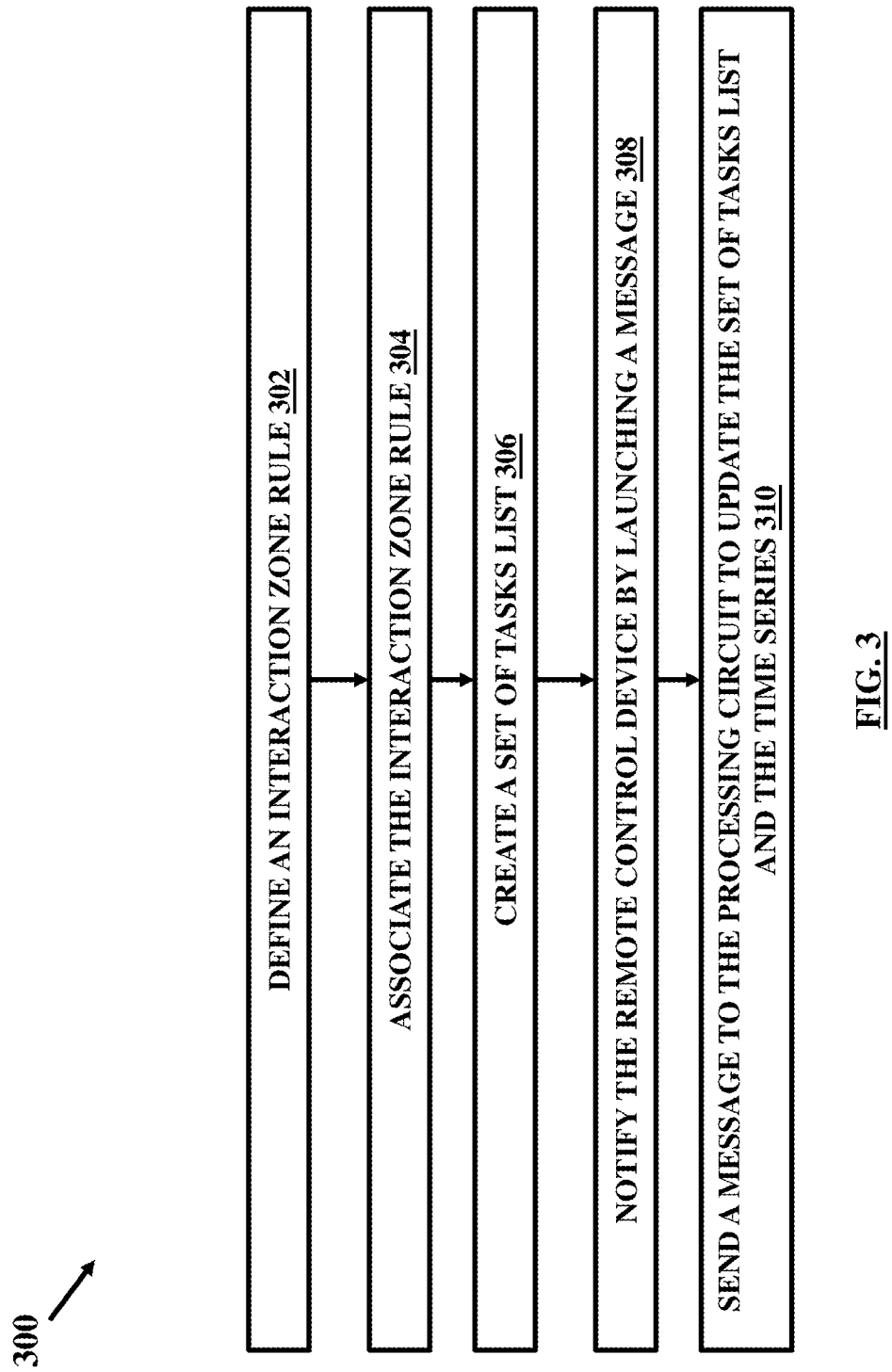
FIG. 3 illustrates a method flowchart for facilitating scheduling and performance of a healthcare task, in accordance with an embodiment herein.

FIG. 3, with reference to FIGS. 1A through 2, illustrates a method flowchart 300 for facilitating performance of a healthcare task, in accordance with an embodiment herein.

The method may include defining an interaction zone rule at step 302. For example, the defining of the interaction zone rule may include defining a time series. The method may further include associating the interaction zone rule for one or more participants at step 304. In an example, the associating of the interaction zone rule may include associating the current time occurrence and the future time occurrence on the time series. In an example, the future time occurrence may be associated with next time event occurrence schedule. For example, the future time occurrence may refer to a point on the time series when an event occurs next time such as when the remote control device 104 is detected to be present in the interaction zone 108 next time or when the weather sensor 214 detects a weather controlled triggering event next time relative to the current time occurrence on the time series. In various examples, the interaction zone rule may be based on weather-related events, location, time, and the like parameters.

At step 306, the set of tasks list is created by the processing circuit 110. The tasks list has been described above in conjunction with FIG. 2. Each tasks list is associated with the third identification code. Further, each task within the tasks list may be associated with a fourth identification code that is indicative of the task and the tasks list that contains the task. In an example, the tasks and the tasks list may be associated and mapped with the triggering events in accordance with the set of rules defined by the rules engine 216. For example, the tasks list may be sliced into tasks or a group of tasks for different triggering events that necessitate scheduling of the tasks or group of tasks from the tasks list. Each such mapped task or group of tasks may be associated a fifth unique identification code that is indicative of the group of tasks and the corresponding triggering event.

The processing circuit 110 establishes the set of rules that defines scheduling and performance of a task from the set of tasks based on occurrence of a triggering event. In view of the established rules, when a triggering event occurs and a related input is received from the event monitor 210 by the processing circuit 110, the processing circuit 110 may notify the remote control device 104 by launching an activation message that is displayable on the remote control device 104 at step 308. The activation message includes an instruction to inform the practitioner to perform the task at the future time occurrence upon occurrence of the triggering event in accordance with the established rule.

Once the task is performed by the practitioner at the future time occurrence, the remote control device 104 may send a message to the processing circuit 110 to update the set of tasks list and the time series automatically and dynamically based on performance status of the task by the practitioner at step 310. In case the task is successfully performed, the current time occurrence replaces the future time occurrence and a new future time occurrence is defined on the time series based on an input from the remote control device that is indicative of a health status of the patient.

An embodiment herein provides a computer-implemented method for scheduling, tracking, and executing performance of the set of tasks. The processing circuit 110 may define the time series. The processing circuit 110 may associate the current time occurrence on the time series and the future time occurrence on the time series. The future time occurrence may be defined as a succeeding time occurrence on the time series in relation to the current time occurrence. For example, the future time occurrence may be associated with the next time the triggering event occurs, in an example. In an example, the future time occurrence may be associated with the next time a practitioner visits the interaction zone or the next time a defined temperature, humidity level, or rain is sensed by the event monitor in the interaction zone. The processing circuit 110 may create a tasks list including the set of tasks. The tasks list may include an actionable questionnaire, a test plan, a process verifier, a runbook, a careplan, a regulatory mandate that each may be editable and executable at the future time occurrence. In an embodiment, the future time occurrence may be defined with respect to the triggering event so that when the triggering occurs after a defined number of times or next time, the future time occurrence is noted by the processing circuit 110 to allow the set of tasks to be executed. The execution and performance of the tasks may be locked until the defined future time occurrence. The set of tasks included within the work list may remain pending till the future time occurrence. The performance and execution of the tasks based on associated future time occurrence or the time series and the triggering event may be initiated based on the interaction zone rule as identified by the processing circuit 110 through user defined parameters. The interaction zone rule may include defining a plurality of triggering events, by the processing circuit 110, to initiate the set of tasks. For example, the interaction zone rule may define execution of the set tasks in a specific series when a specific weather controlled event is detected at the future time occurrence within the interaction zone. In an example, the interaction zone rule may define execution of the set of tasks in a specific series when the spatial presence of the remote device is detected within the interaction zone at the future time occurrence. In various other embodiments, the interaction zone rule may be defined in accordance with different governing parameters.

The processing circuit 110 may associate the interaction zone rule with one or more participants including a health practitioner, a patient, and the like. For example, the interaction zone rule may be custom defined specific to a patient and associated healthcare practitioner. The patient and the health practitioner may be identified through identification codes executable by the processing circuit 110. The processing circuit 110 may schedule a task from the set of tasks at the future time occurrence relative to the current time occurrence based on occurrence of the triggering event in view of the interaction zone rule. The control server may receive a signal indicative of an output from an event monitor. The output signifies the triggering event at the future time occurrence. The processing circuit 110 processes the signal and notifies the remote device for performance of the scheduled task at the future time occurrence upon detection of the triggering event. The step of notifying may include generating an electric signal comprising data signifying the schedule task and instructions for performance of the scheduled task, transmitting the electric signal from the control server, communicatively connected with the special purpose processing circuit 110, in a network comprising a plurality of communicatively linked data communication devices, converting the electric signal into a plurality of pixels, and displaying the plurality of pixels on a display unit of the remote device to launch an activation message that includes an instruction to perform the task at the future time occurrence upon occurrence of the triggering event in accordance with the interaction zone rule. Once the task is performed by the healthcare practitioner or a medical device, the remote device may generate a signal indicative of performance status of the task and health status of the patient. The signal may be transmitted to the control server. The control server may receive a message from the remote device to update the set of tasks list and the time series dynamically based on performance status of the task. For example, the set of tasks lists may be modified to consider the task having performed and updating the time series accordingly. This may include replacing the current time occurrence by the future time occurrence and defining a new future time occurrence on the time series based on the performance status of the task and an input from the remote device that is indicative of health of a patient. The new future time occurrence may be defined to be executed in accordance with the interaction zone rule but may be dynamically updated even before the execution of next task occurs. The dynamically updates can be done based on the health status of the patient, recommendation from the remote device or associated health practitioner and the like.

In an example, the interaction zone rule is applied in association with an interaction zone defined by physical coordinates of a geographical location such that the triggering event is indicative of an entry of the remote device within the geographical location bounded by the physical coordinates at the future time occurrence. The spatial presence of the remote device within the interaction zone may be detected with the use of a location sensor physically located within the interaction zone or associated with the remote device and capable of detecting transition of the remote device from outside to within the interaction zone.

In an example, the interaction zone rule is applied in association with an interaction zone defined by physical coordinates of a geographical location such that the triggering event is indicative of a weather controlled event occurrence within the geographical location bounded by the physical coordinates at the future time occurrence. The monitoring of weather parameters or the weather-controlled triggering event may be done with the use of a weather sensor physically located within the interaction zone or associated with the remote device and capable of sending detected signals indicative of the weather-controlled triggering event to the control server. The weather-controlled triggering event may include such as rain, humidity, and temperature, and the like such that the weather sensor may include a rain sensor, a temperature sensor, and a humidity sensor. The weather sensor may be capable of sending signals to the control server indicative of occurrence of the weather-controlled triggering event only at the future time occurrence.

The method steps discussed above may be executed with the use of a computer-controlled system for scheduling, tracking, and executing performance of the set of tasks that may include the control server. The control server may be configured to communicatively connect with the remote device through a network for allowing exchange of computer executable patient data between the control server and the remote device. The system may include the processing circuit 110 included within or communicatively connected with the control server. The processing circuit 110 may be configured to define the time series, associate a current time occurrence on the time series, and associate a future time occurrence on the time series. The processing circuit 110 may create a tasks list including the set of tasks. The processing circuit 110 may define the interaction zone rule in association with the time series, associate the interaction zone rule with one or more participants, and schedule a task from the set of tasks at the future time occurrence relative to the current time occurrence based on occurrence of a triggering event in view of the interaction zone rule. The processing circuit 110 may be configured to receive an input indicative of the triggering event at the future time occurrence. The processing circuit 110 may notify the remote device for performance of the scheduled task at the future time occurrence upon detection of the triggering event. The processing circuit 110 may be configured to receive a message from the remote device to update the set of tasks list and the time series dynamically based on performance status of the task. The computer-controlled system may include the event monitor comprising a location sensor and a weather sensor communicatively connected with the control server for detecting spatial presence and a weather controlled event respectively upon occurrence of the triggering event.

The computer-controlled system further comprising an electronic medical records database communicatively connected with the control server. The electronic medical records database stores computer executable patient data files. Each of the computer executable patient data files is associated with a first identification code that is indicative of a patient's identity, a second identification code that is indicative of a practitioner associated with the patient, a third identification code that is indicative of a set of tasks recommended for performance, in association with the patient, by the practitioner at the current time occurrence. In an example, the current time occurrence is associated with a last visit of the practitioner in the interaction zone for the patient. In an example, the future time occurrence is associated with occurrence of the triggering event such that the future time occurrence is set to occur after a predefined number of the triggering event has occurred within the interaction zone. The predefined number is dynamically adjusted by the processing circuit 110 based on an input received from the remote device including a computer executable file signifying health status of the patient and a recommendation note by the practitioner. The interaction zone is defined to exhibit preset capabilities within a defined spatial coordinate of a geographical location to allow information exchange between the control server and the remote device within the interaction zone. The performance of the set of tasks is limited within the spatial coordinates of the interaction zone in view of the interaction zone rule.

The embodiments herein provide several advantages. For example, if a healthcare practitioner visits an elderly patient for routine checkup, glucose monitoring, blood analysis, blood pressure check etc and something is required from the patient but the practitioner may not want it done all the time or make a special trip for it, the embodiments herein may let the practitioner setup the tasks list and then establish a rule that next time when a triggering event occurs at specific conditions; e.g. entering the facility or going of a patient to home, or when patient arrives and checks in the hospital, a task or a groups of tasks are driven.

The embodiments herein define a correlation between spatial or weather-related coordinates and the set of tasks using the set of rules from the rules engine 216 to generate health management guidelines and performance or scheduling of healthcare tasks contained within the tasks lists for several patients.

The embodiments herein associate the next time occurrence of a triggering event so as to ensure priority tasks are scheduled next time when the triggering event occurs. Accordingly, based on available healthcare resources and requirements, priority ratings may be associated with the different tasks scheduled to occur with respect to different patients or on the same patient. Based on the priority ratings, the time series is dynamically updated for multiple tasks associated with future time occurrences for the same patient or different patients. For example, a task which holds a higher priority rating based on defined constraints and parameters may be scheduled to occur next time the triggering event occurs and accordingly is associated with the next future time occurrence of the triggering event for the patient in combination with a practitioner scheduled to perform the task.

The embodiments herein may be used in healthcare industries. Alternatively, the embodiments herein may be used in other industries. For example, when a sales person or a company representative visits the interaction zone 108 next time, the processing circuit 110 may trigger the remote control device 104 to perform a defined set of tasks or execute a specific work list or task list. In another example, when a maintenance engineer visits the interaction zone 108 for dealing with water heating issues in a building, the processing circuit 110 may trigger the remote control device 104 to perform some additional tasks for other maintenance issues of the building at the future time occurrence.

In accordance with some embodiments, methods and systems are discussed hereafter for creating and managing the work lists (or tasks lists used interchangeably without limitations).

Figure 4:
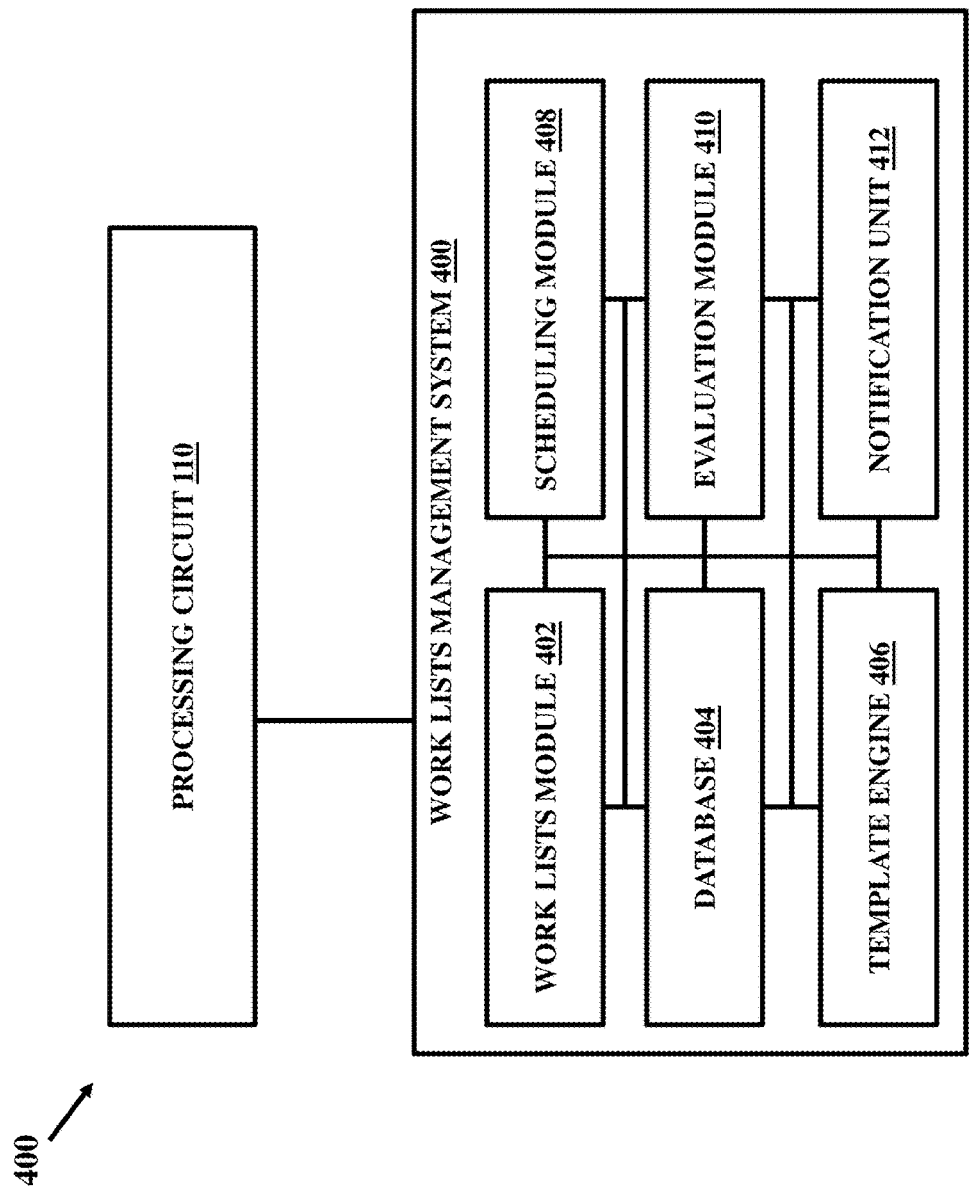
FIG. 4 illustrates a block diagram of a work lists management system communicatively coupled with a processing circuit or a processor, in accordance with an embodiment herein.

FIG. 4, with reference to FIGS. 1A through 3, illustrates a block diagram of a work lists management system 400 (or tasks lists management system 400 or system 400 simply used interchangeably without limitations) for managing the work lists communicatively coupled with the processing circuit or the processor 110 (referred to herein interchangeably without limitations. The system 400 may include a work lists module 402 for creating a work list with necessary tasks. The system 400 may further include a database 404 containing a set of libraries as will be discussed hereafter. The libraries may be used to pick predefined tasks for generating the work lists or editing the work lists or for executing runnable scripts. The system 400 may further include a template engine 406 for generating work lists of defined nature such as check lists, care plans, questionnaires and the like. The template engine 406 may further provide design tools to generate work lists of specific designs. A scheduling module 408 processes scheduling tasks and accordingly tie different tasks of the work lists on a time series and identifies timelines associated with the different tasks. An evaluation module 410 examines status of the tasks on the time series and generates an automated output indicative of tasks status. A notification unit 412 automatically notifies other systems about status of the tasks as soon as they are complete or if they are pending after due time.

In an embodiment, the system 400 can be configured to be included within the processing circuit 110 or coupled with the processing circuit for performing one or more functions of the processing circuit 110 as discussed in conjunction with FIGS. 1A through 3. In an embodiment, the system 400 may perform one or more functions performed by the tasks lists engine 208. In an embodiment, the system 400 may perform one or more functions performed by the rules engine 216. In an embodiment, the system 400 may perform one or more functions performed by the time series module 206.

Figure 5:
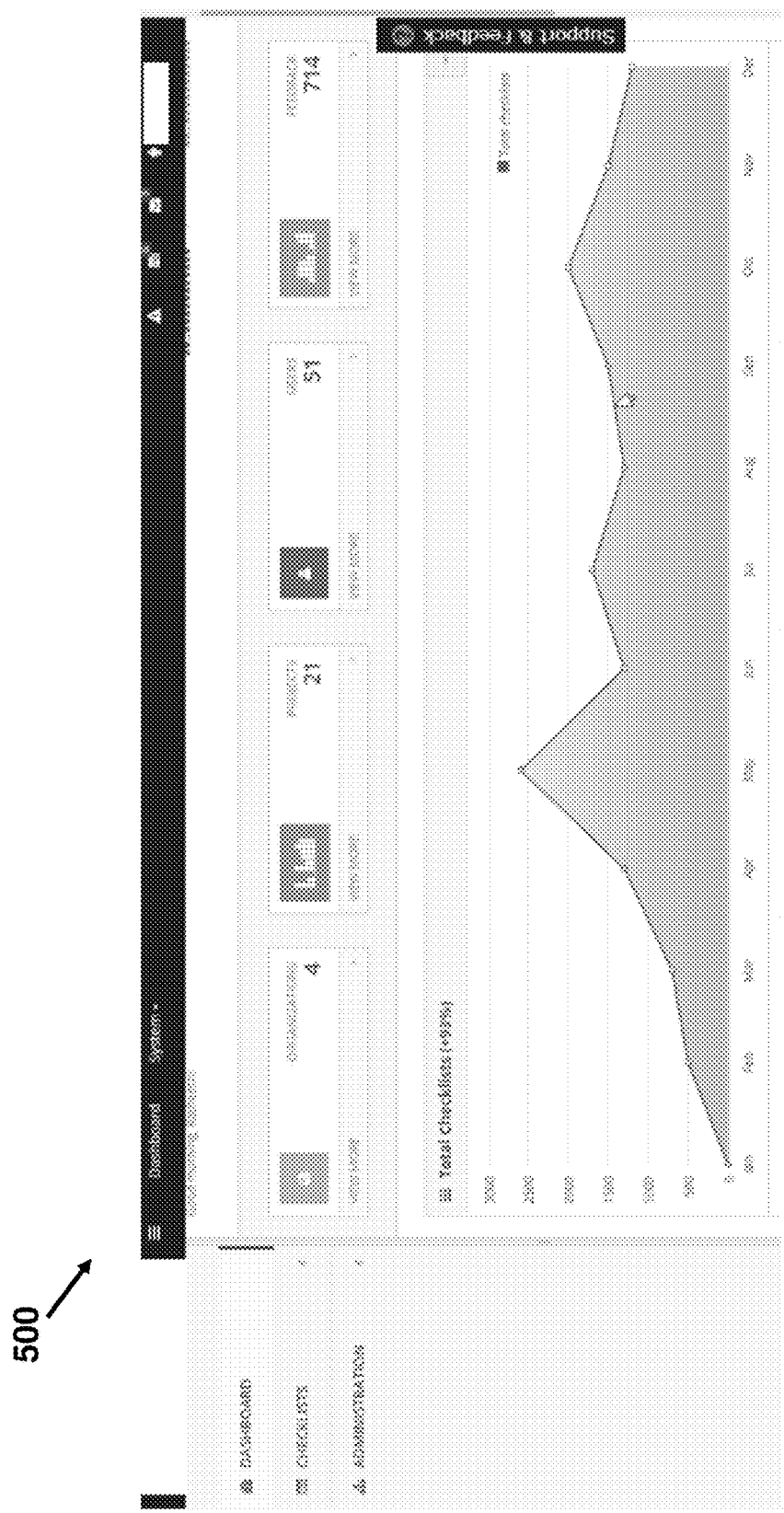
FIG. 5 illustrates a dashboard configured to provide an interface for interacting with the work lists management system to allow a user to navigate through different options for work lists creation and management, in accordance with an embodiment herein.
Figure 6:
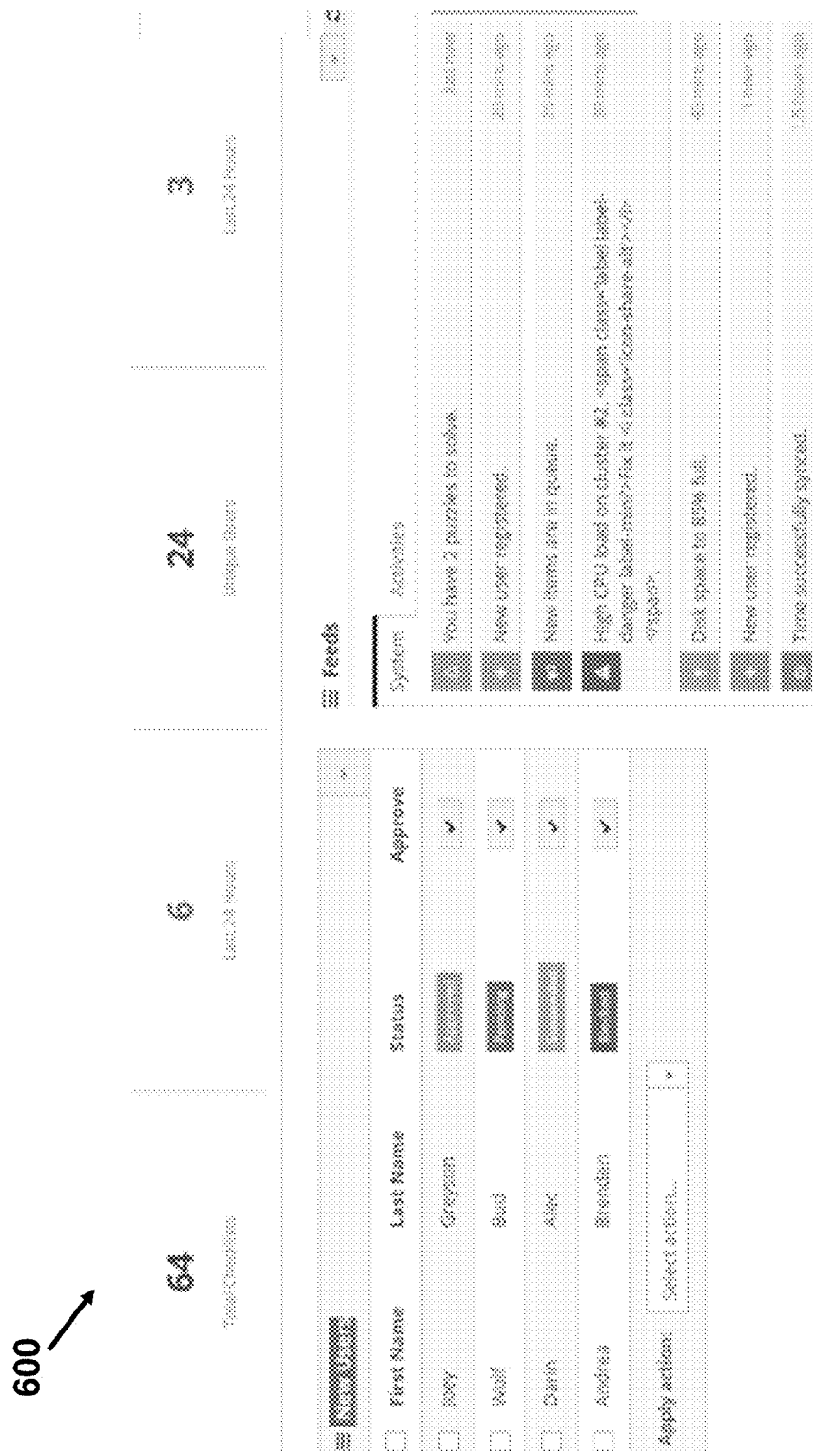
FIG. 6 illustrates another interface that provides detailed information about check lists or work lists associated with a user who attended in defined time duration, in accordance with an embodiment herein.

FIG. 5, with reference to FIGS. 1A through 4, illustrates a dashboard 500 configured to provide an interface for interacting with the system 400 to allow a user to navigate through different options for work lists creation and management facilitated by the system 400. As depicted, the dashboard 500 presents assigned organizations, projects, users, and feedback options for a particular user. The dashboard 500 further presents details about checklists or work lists associated with the user. FIG. 6, with reference to FIGS. 1A through 5, illustrates another interface 600 that provides detailed information about the check lists or work lists associated with the user attended in defined time duration for example last 24 hours and the like. The interface 600 further depicts list of tasks that form a part of the checklists or the work lists assigned to the user or being executed by the user.

Figure 7:
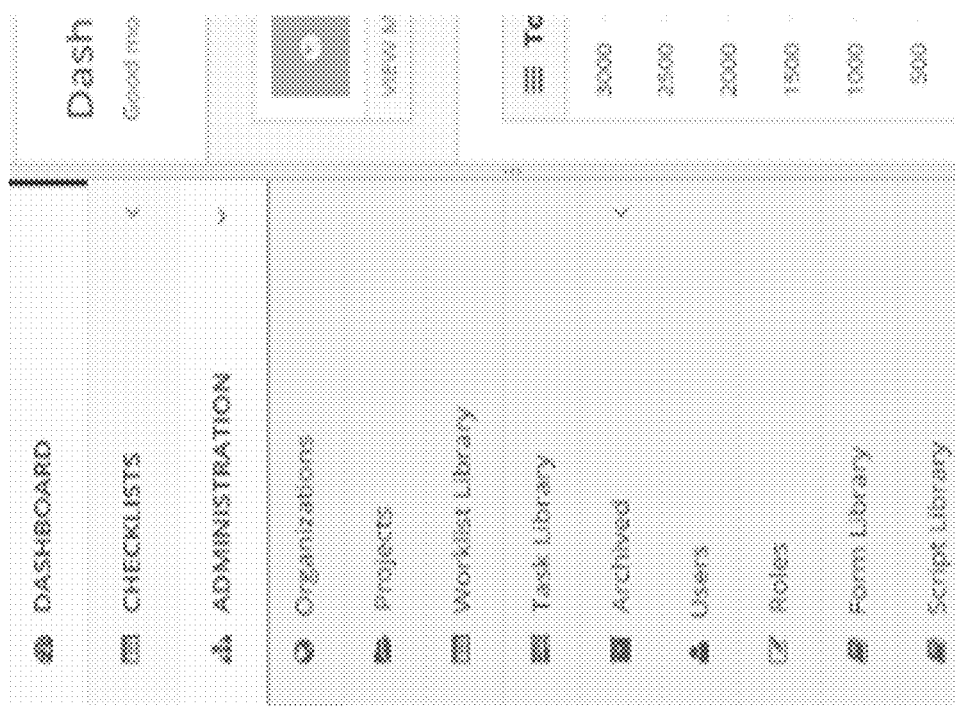
FIG. 7 illustrates another section of a user interface that provides libraries and tabs for accessing various libraries contained within the work lists management system, in accordance with an embodiment herein.
Figure 8:
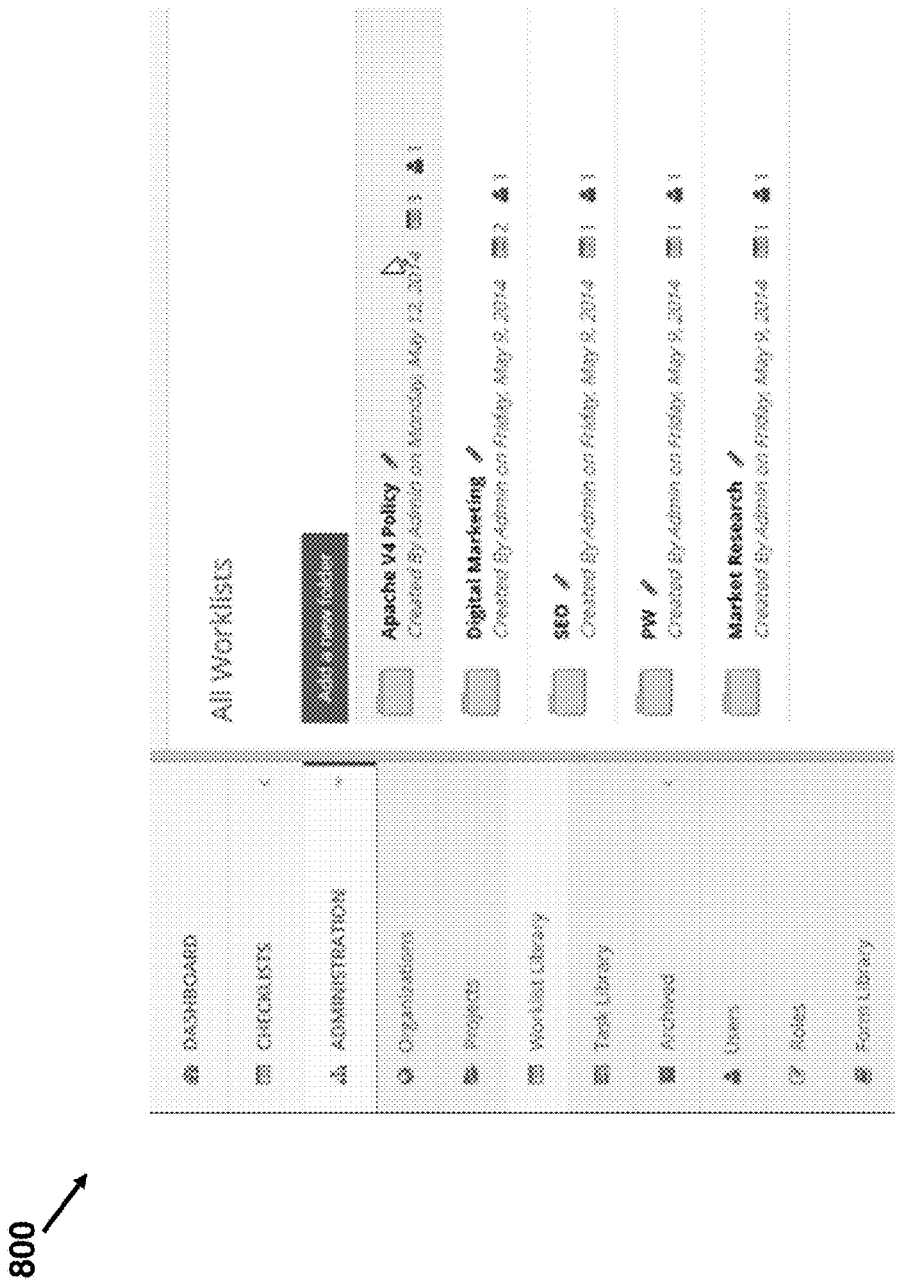
FIG. 8 illustrates another section of a user interface that provides libraries and tabs for accessing various libraries contained within the work lists management system, in accordance with an embodiment herein.

FIG. 7, with reference to FIGS. 1A through 6, illustrates another section of a user interface 700 that provides tabs for accessing various libraries contained within the system 400. The libraries may include a projects library, a work lists library, a task library, a roles library, a form library, a script library, a reference library, and the like. As depicted in FIG. 8, with reference to FIGS. 1A through 7, the work lists library 800 contains different folders or work lists assigned to a user. New work lists can be created under this library or existing work lists can be edited by authorized persons. The task library allows defining tasks or selecting or editing tasks for a work list. In an example, the task library may include predefined tasks that may be used directly for the wok list. A user may for example pick a task from the task library based on a category of the task such as software, networking and the like and add it to the work list in the time series. The form library includes well defined forms that may be imported to a work list. The role library includes various roles with defined access priorities. The script library includes runnable codes or scripts for executing a particular task. For example, after a task is complete, an underlying script for the task may automatically trigger a notification to be sent to other systems.

The system 400 allows accounts to be setup for users to create the work lists. The system may facilitate trainings or tutorials for the users or those who execute the work lists. The system 400 may allow to create entities that may execute the work lists, to set work lists nature, to run the work lists once or multiple times, to run the work lists as an anonymous user, to run the work lists as an authenticated user, to add time stamp or time series to the work lists, to invite an outside party to view or run or perform one or more tasks on the work lists, to allow subscribers for the work lists, to export the work lists, to import the work lists from outside the system, to set the work lists reminders, to create and edit work lists templates, to schedule the work lists, to generate calendar invites, to make the work lists public, to define the work lists as tasks lists or processes, or procedures, or test plans, or care plans, or protocols, to create embedded work lists, to add folders to form libraries of the work lists, to create citations for the work lists, to specify a license of any of the work lists, to allow one or more entities to execute the work lists associated to them, to collaborate among one or more work lists, to post comments on execution of the work lists, to handle notifications, to provide reporting or feedback, to organize the work lists, to analyze life cycle behavior of the work lists, and to perform various other functions associated with the work lists.

The system 400 for managing the work lists is a collaborative protocol documentation, automation and compliance platform configured to facilitate distributed safety critical systems. The system 400 documents, tracks and analyzes the tasks or work lists such that the work lists may be defined for a single person, organization or system. In another embodiment, the system 400 documents, tracks and analyzes the tasks or work lists such that the work lists may be defined to be distributed across people, organizations or systems.

In an example, the system 400 may provide regulated industries with an enterprise-grade integration-friendly solution which may ensure that all processes, procedures, compliance requirements associated with well-defined protocols in an organization are done in an intended sequence by required personnel within a specified time period. The regulated industries may for example comprise a healthcare industry and the like. The system 400 may track and ensure proper execution. In an embodiment, the system 400 may facilitate define processes and the work lists that may be scalable, repeatable and provable.

The system 400 may find use in a variety of applications so as to manage tasks through the use of the work lists creation and management. The system 400 may be configured to be used as a flexible tool for creating the work lists as care plans, test plans, questionnaires, process verifiers, medical care plans, regulatory mandate checkers, process verifiers, surveys, complex check lists, and the like. The system 400 may provide an easy verification mechanism of regulatory compliance requirements. The system 400 may be configured to facilitate in-built process improvement with user feedback. A user can provide feedback in the form of ratings to improve the work lists and their management.

The system 400 may be configured to use the work lists to capture behavior of patients or other entities in a setup by running surveys using the work lists. The system 400 may be used to carry standard operating procedures using the work lists as run books. The system 400 may be used to allow complex care plans to be created and coordinated across complex distributed organizations wherein the organizations may be tied and coordinated at patient level using internet-based user configurable APIs. With the use of user configurable APIs, it is easy to design and run care plans or test plans. The system 400 may ensure proof of compliance. The system 400 allows automate regulated protocol execution across clinical organizations and protocols. The system 400 ensures that organizational processes are being followed. The system 400 ensures health of servers by running scheduled work lists periodically by operations team in an organization.

The system 400 allows scheduling the work lists and reminding users to run them. In an embodiment, the system 400 may send notifications to for example IT personals to inform that a particular work list is due to be run and the like so as to ensure that the work lists are run. The system 400 may allow versatility by allowing its users to add comments, add attachments and screenshots, add runnable scripts, perform conditional runs, and add adhoc/procedural work lists and the like. The runnable scripts may be triggered to run at a defined event such as at the end of a work list or at the end of a task. The conditional runs may allow altering the order in which several tasks of a work list are executed. The procedural work lists allow running the tasks of a work list in a defined order and the adhoc work lists allow running the tasks of a work list in any order as preferred by a user.

The system 400 may allow exporting the work lists as PDF, Excel, and the like. In an embodiment, the system 400 may allow to import the ready-made work lists into the system 400. In an embodiment the work lists can be generated and assigned to staff member across multiple organizational boundaries. Exemplary use cases in accordance with some embodiments of the work lists management system 400 are provided hereafter. The system 400 may allow front desk personnel in hospitals to run appointment procedures based on pre-defined instructions for the type of admission such as procedure, regular, or emergency. The system 400 may allow procedure room personnel in hospitals to prepare for procedures by referring to instructions defined by the work lists. The system 400 may allow care transitions. The system 400 may allow preventing of medication errors. The system 400 may allow hospitals to cut costs by making sure that doctors stick to guidelines. The system 400 may provide a complete set of tools to model, implement, and automate medical processes such as treatment and drug administration.

The system 400 may allow pulling data from disparate IT systems including such as HIS or EMR systems to streamline patient information flow keeping it accessible for doctors and other healthcare providers. In accordance with some embodiments, required steps may be executed across multiple distributed systems such as EHRs, lab equipment, digital pathology, imaging devices, or other devices or even manual procedures.

The system 400 may provide patients with chronic conditions an ability to manage their health from the comfort of their home using next generation monitoring and wearable systems. The system 400 may acquire data from an EMR and send prescriptions to a hospital pharmacy or other related entities automatically. The system 400 may send notifications that may alert medical staff so that necessary tasks or work lists are not left uncompleted and quality of care is not compromised. The system 400 may allow patients to use various kinds of care plans that they may want to subscribe to such as losing weight, stopping smoking, managing their diet, handling exercise plans and the like. The system 400 may allow the work lists to act as questionnaires helping doctors collect information from patients before administering their care plan.

The system 400 may allow the care plans, work lists, protocols, processes, and procedures to be created and packaged in modules that can be commercialized for use as modular applications to manage or run specific work lists for specific functions and tasks in a specific setup. The system 400 may allow medical data to be kept safe from unwanted exposure with integral permissions across the system using process roles to control data access. The system 400 may allow automating regulated protocol execution across organizations and protocols.

The system 400 may allow capturing medical device FDA classes such as FDA Class I, II or III device development, testing, or deploying processes, consistent execution, monitoring, exceptions, and optimizing the processes. This may facilitate in improving regulatory compliance filings such as 510K thereby bringing cost benefits and improving time to market for new patient diagnostic and therapeutic devices and the like.

The system 400 may facilitate Biotech or Life Sciences firms in documentation or other compliance requirements for clinical trials or other drug research tasks, reducing administration costs and burdens. The system 400 may allow operations team to ensure that routine procedures and operations are carried out. The system 400 may allow ensuring that organizational processes are being followed during design, development, testing, documentation, and maintenance. The system 400 may allow designing checklists to ensure that all features are implemented. The system 400 may allow defining the checklists to verify that all product deliverables are complete.

Figure 9:
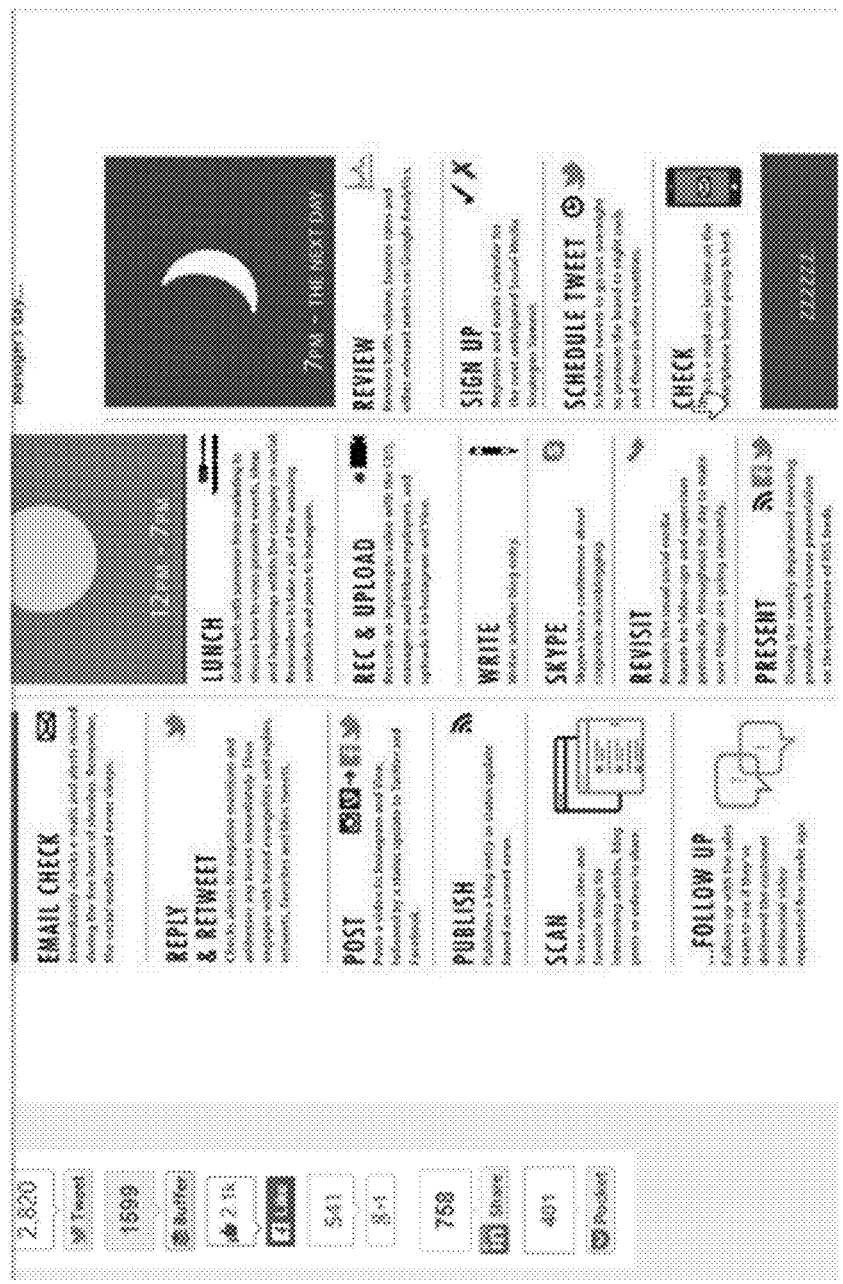
FIG. 9 depicts exemplary activities that may be managed with the use of the work lists management system, in accordance with an embodiment herein.

The system 400 may allow defining SEO (Search Engine Optimization) checklists that list aspects of marketing to be taken care of. The system 400 may allow defining product launch checklists that list out various aspects to be taken care of during product launch. The system 400 may allow creating test plans with expected outcomes. The system 400 may facilitate maintaining of high level of service even when procedures are changed or a new procedure is implemented. The system 400 may allow organizing and carrying out repetitive tight schedules. As an example, an interface 900 is depicted in FIG. 9, with reference to FIGS. 1A through 8, displaying activities of a social media manager that may be managed with the use of the work lists management system 400, in accordance with an embodiment herein. The various tasks or activities of the social media manager may be run through the system 400 by the social media manager on a regular basis for example or as prescribed.

Figure 10:
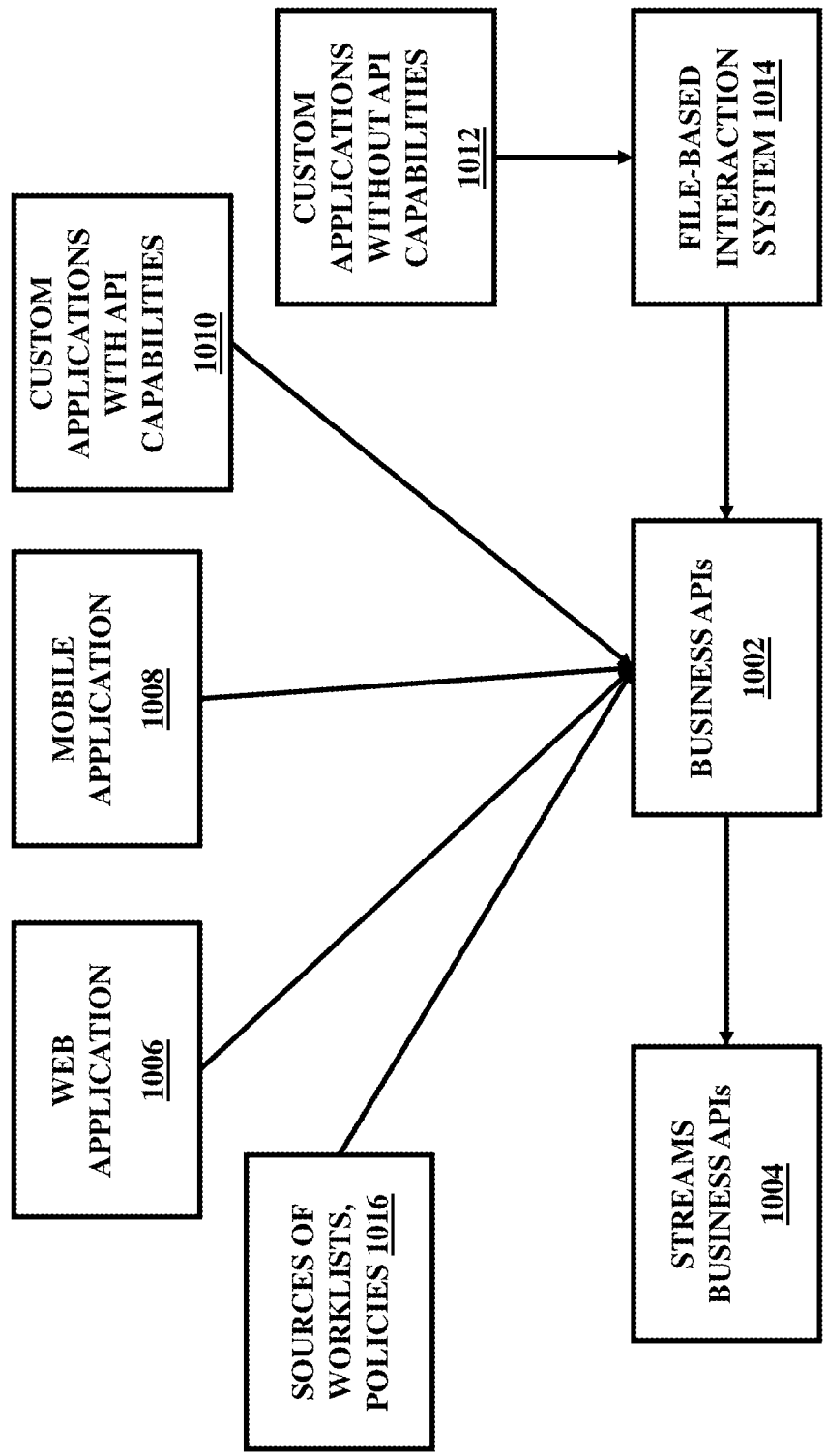
FIG. 10 illustrates different components of architecture of a work lists management system that may provide a distributed arrangement and functionality of work lists management across a plurality of organizations or across a plurality of departments in a single organization, in accordance with an embodiment herein.
Figure 11:
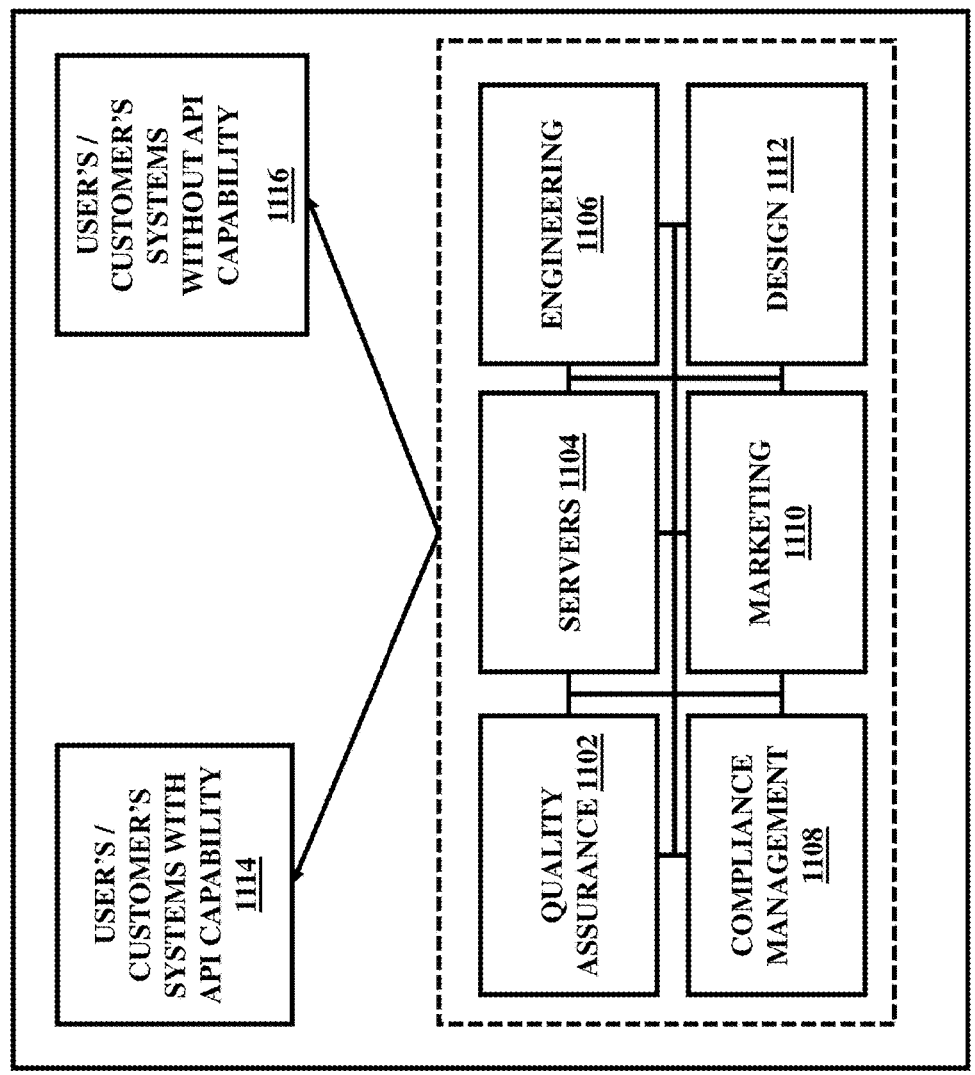
FIG. 11 illustrates components of a system architecture according to an embodiment herein.
Figure 12:
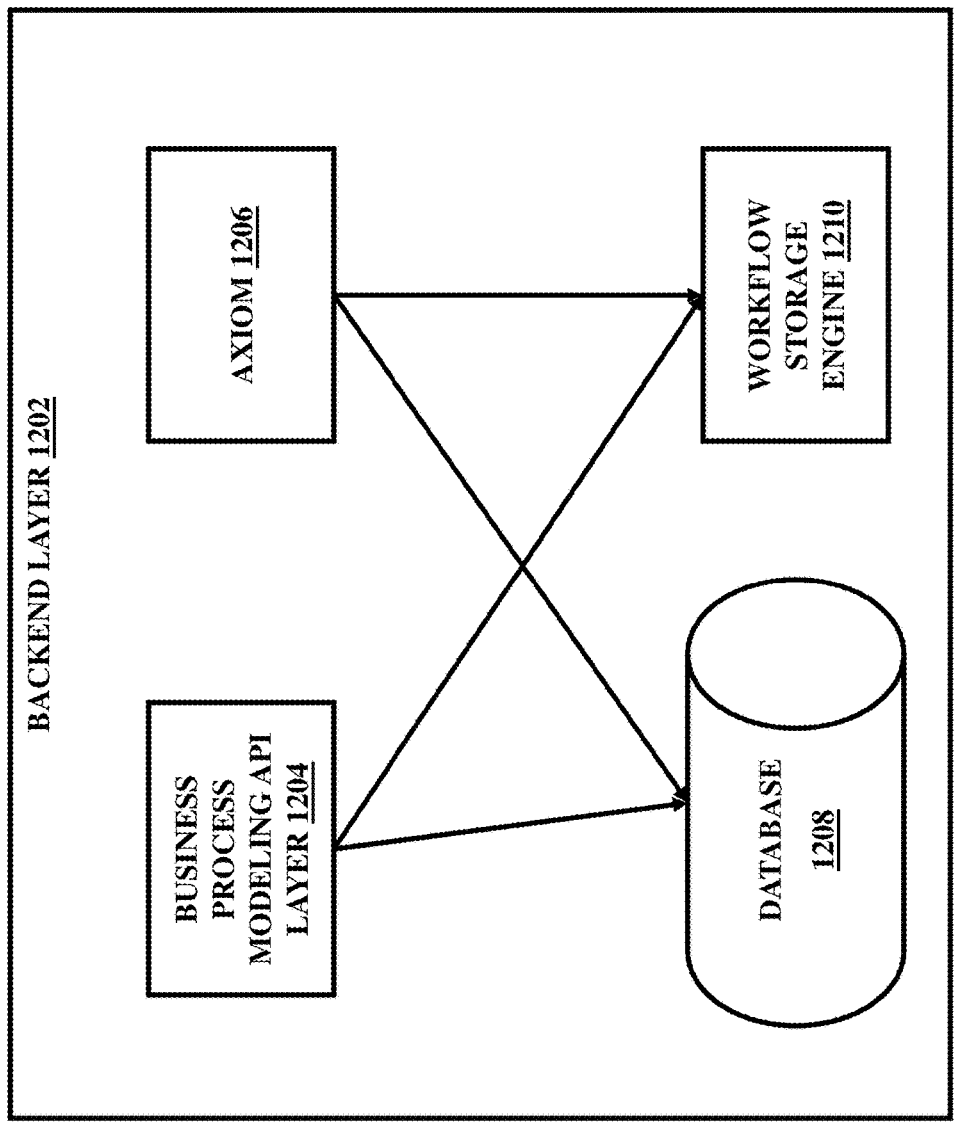
FIG. 12 illustrates components of a system architecture according to an embodiment herein.

FIGS. 10 through 12, with reference to FIGS. 1A through 9, illustrate different components of architecture of the work lists management system 400 that may provide a distributed arrangement and functionality of work lists management across a plurality of organizations or across a plurality of departments in a single organization, in some embodiments herein. The different components illustrated in FIGS. 10 through 12 may be integrated or interconnected through various communication and networking channels for allowing flow of information across the entire system 400 in the architecture.

FIG. 10 illustrates, among other things, an API layer including a set of APIs (Application Programming Interfaces) that serves as a foundation to define the interaction zone 108. The APIs may include Business APIs 1002 and Streams Business APIs 1004. The API layer connects with an application layer that may include a web application 1006, a mobile application 1008, custom applications with API capabilities 1010, and custom applications without API capabilities 1012. A file-based interaction system 1014 may be provided to interact with custom applications without API capabilities 1012 and Business APIs 1002. The tasks lists or work lists may be designed or executed at the API layer such as through the business APIs. The application layer and the API layer may allow a user to write a user application that may involve designing of specific work lists executable by the work lists management system 400. In an example, execution of the user application may involve multiple processes distributed across multiple participants. The application involving the work lists or check lists or tasks lists may be defined such that the processes or different tasks may be associated with timelines and monitored for completion. The user application executable by the work lists management system 400 may collaborate among the distributed participants. The user application designed by the user may be integrated within the work lists management system 400 such as shown in FIG. 11 through the use of distributed execution servers connected operatively with a plurality of devices. In an example, sources of work lists and policies 1016 may be associated with the business APIs 1002.

FIG. 11 shows different participants that may execute one or more processes of a work list design by the user facilitated through the API layer and the application layer and that may be allowed to be integrated within and executed by the work lists management system 400. The distributed participants or systems may involve such as quality assurance team 1102, servers 1104, engineering team 1106, compliance management team 1108, marketing team 1110, and design team 1112. Each of the distributed participants may perform specific processes or tasks from the work list. The interaction zone 108 may be defined among the distributed participants so that monitoring of performance of the specific processes is done based on different rules defined to manage interaction among the distributed participants upon occurrence of triggering events within the interaction zone 108. The interaction zone 108 may define relationships and interaction among the participants and the processes performed by them within the interaction zone 108 in association with a defined work list executed by the work lists management system 400. The interaction may be based on weather, time, location, and the like parameters. The processes may be performed when a triggering event occurs within the interaction zone 108 and accordingly the different processes may be allocated and collaborated among the participants by the work lists management system 400. In an example, the web application 1006 and the mobile application 1008 are run on the user end where the work lists may be designed. In an example, the web application 1006 and the mobile application 1008 may be located remotely. The business APIs 1002 may be centralized or may be distributed. The business APIs 1002 may be located within a server hosting the work lists management system 400. Each of the distributed participants may be connected with remote devices such as the device 194 each controlled through an execution server as discussed later.

A user's or customer's systems with API capability 1114 and a user's or customer's systems without API capability 1116 may connect with the API layer, application layer, and the file-based interaction system 1014 for integration of the processes among the distributed participants.

FIG. 12 shows a backend layer 1202 that may interact with the API layer, application layer, file-based interaction system 1014, and the distributed systems, in accordance with some embodiments herein. The backend layer 1014 may include a business process modeling API layer 1204, an axiom 1206, a database 1208, and a workflow storage engine 1210. The workflow storage engine 1210 and database 1208 may store workflows or the work lists. The business process modeling API layer 1204 and axiom 1206 may facilitate workflow or work lists tracking.

Figure 13:
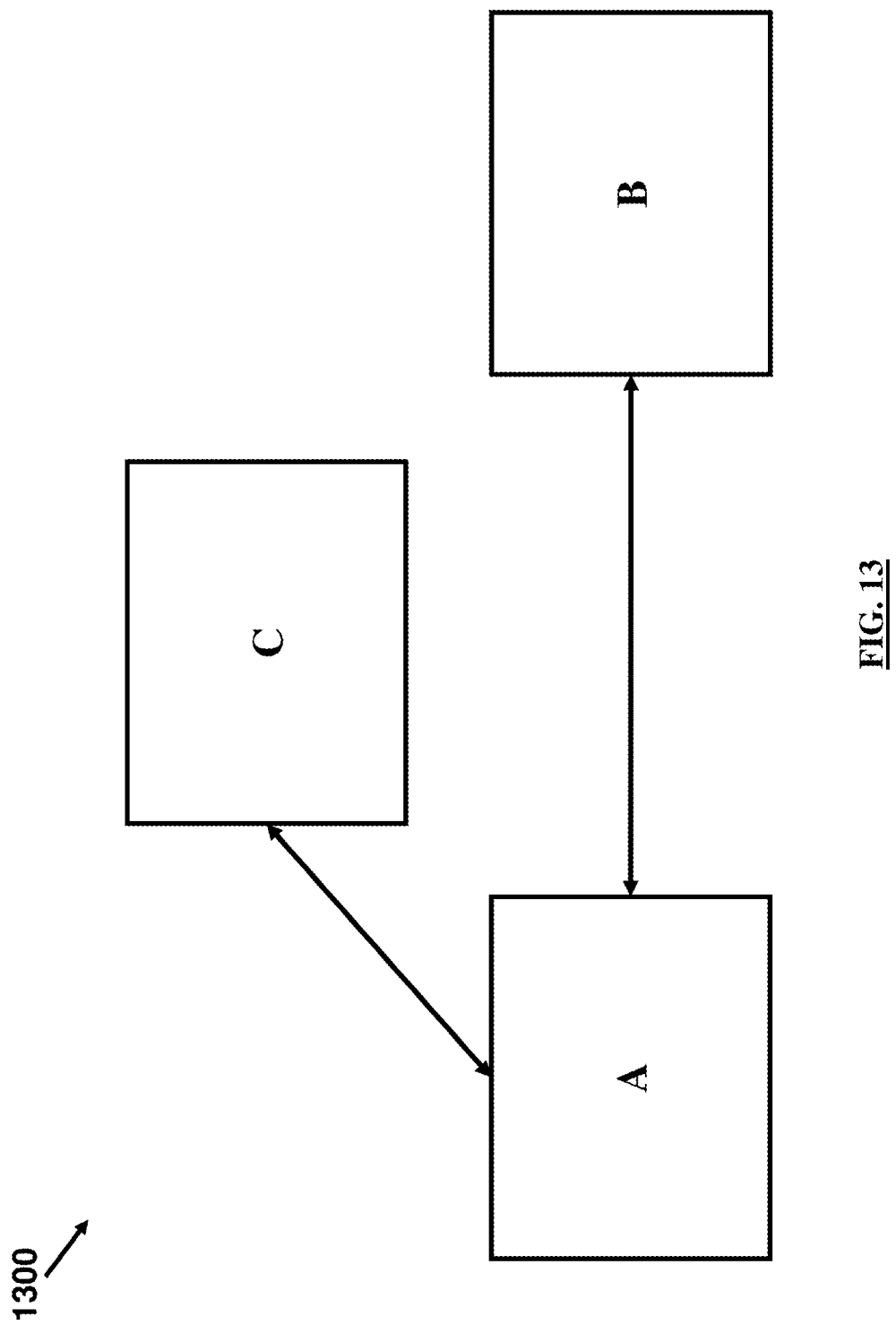
FIG. 13 illustrates an ecosystem and components thereof of a work lists management system interacting with a variety of systems or devices within an interaction zone, in accordance with an embodiment herein.
Figure 14:
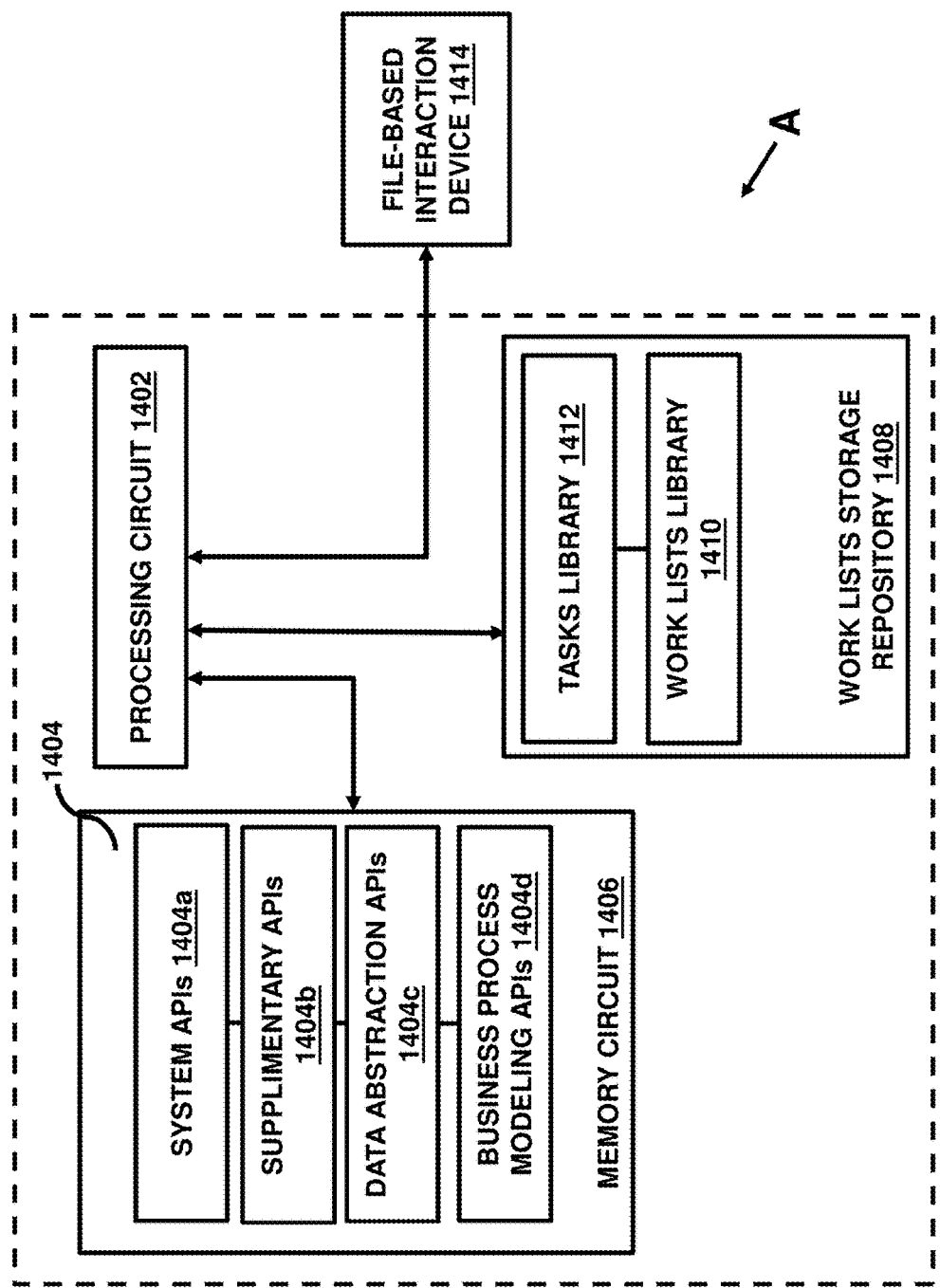
FIG. 14 illustrates components of a system architecture according to an embodiment herein.

FIG. 13 illustrates an ecosystem 1300 of a work lists management system such as the worklists management system 400 interacting with a variety of systems or devices within an interaction zone such as the interaction zone 108, in accordance with an embodiment herein. The ecosystem 1300 may include a section A, a section B, and a section C. The sections A, B, and C are illustrated in FIGS. 14, 15, and 16 respectively in detail.

Figure 15:
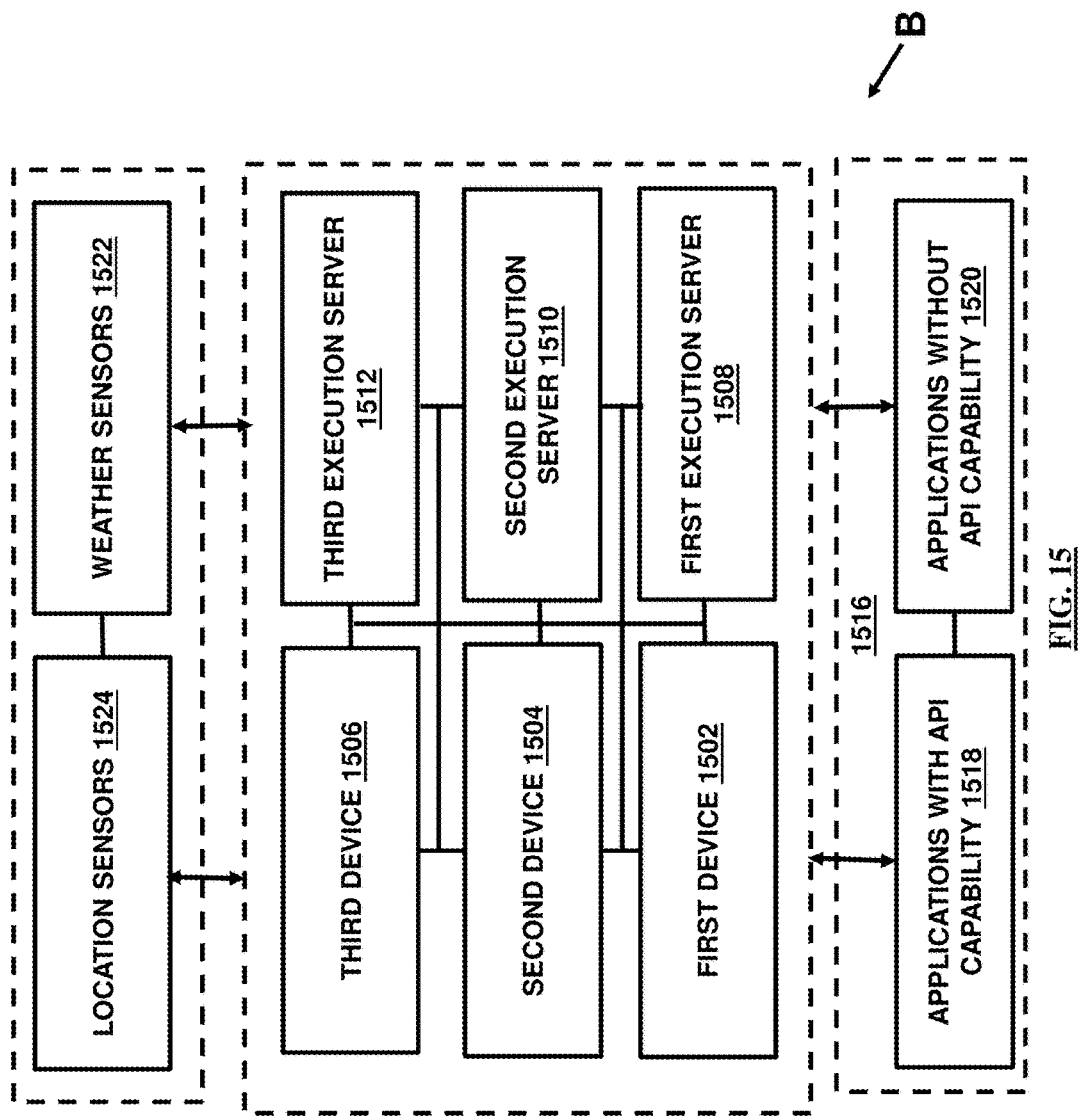
FIG. 15 illustrates components of a system architecture according to an embodiment herein.
Figure 16:
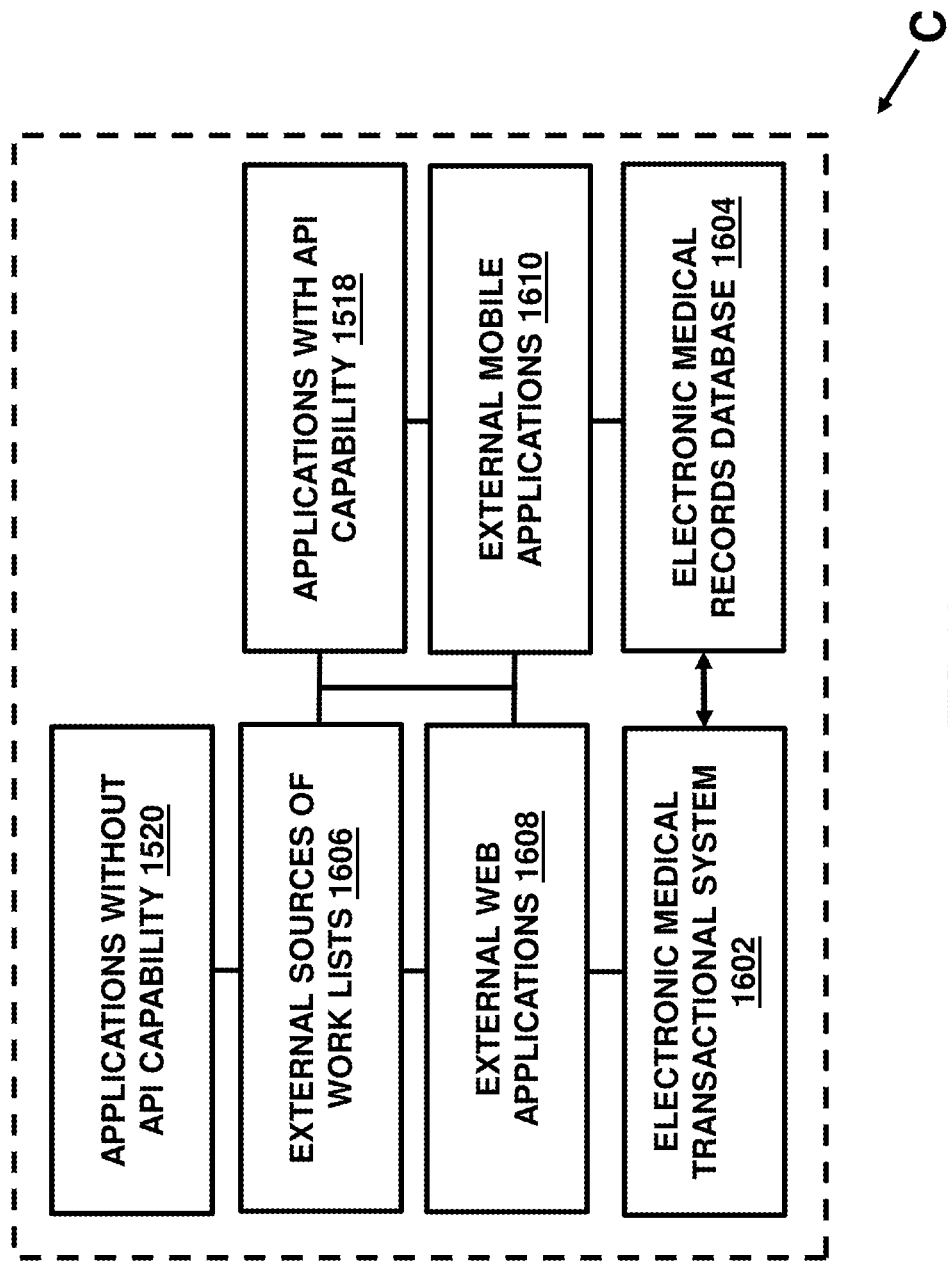
FIG. 16 illustrates components of a system architecture according to an embodiment herein.

Referring to the FIGS. 13-16, the ecosystem 1300 is discussed herein. The section A includes a processing circuit 1402, a stack of API layers including a plurality of APIs 1404, and a memory circuit 1406 storing the APIs 1404, and a work lists storage repository 1408. The processing circuit 1402 is configured to generate a computer executable worklist such as the worklists discussed elsewhere in the document which may include a plurality of tasks similar to the tasks as discussed elsewhere in the document. The tasks may be scheduled to be executed at the future time occurrence on the time series based on occurrence of a triggering event in view of an interaction zone rule. The interaction zone rule may be indicative of a spatial presence and a weather controlled event within the interaction zone 108 as discussed in conjunction with various other figures above. In an embodiment, the plurality of tasks may include a first task, a second task, and a third task. The first task may be executable by a first device 1502, the second task may be executable by a second device 1504, and the third task may be executable by a third device 1506, in accordance with an embodiment herein. The first device 1502 may be controlled by a first execution server 1508, the second device 1504 may be controlled by a second execution server 1510, and the third device 1506 may be controlled by a third execution server 1512 as shown in FIG. 15 such that the first execution server 1508, the second execution server 1510, and the third execution server 1512 are located remote from one another and remote from the processing circuit 1402 in a distributed environment.

Each of the first device 1502, the second device 1504, and the third device 1506 may operate under different interaction zone rules in an embodiment such that for example the second device 1504 may perform the second task upon an entry of the first device 1502 within the interaction zone 108 next time only after the first task is performed by the first device 1502 based on occurrence of a weather controlled triggering event. The interaction zone rule for the second device 1504 in this case may represent spatial presence of the second device 1504 within the interaction zone 108 and association of a sequential task performance with respect to the first device 1502 while the interaction zone rule for the first device 1502 may represent occurrence of a weather controlled triggering event as identified from such as a weather sensor as discussed above without limitations.

The processing circuit 1402 may be communicatively connected with the worklists storage repository 1408. The worklists storage repository 1408 may include a worklists library 1410 containing predefined and user editable worklist templates. The worklist templates may include such as a survey template, a check list template, a care plan template, a questionnaire template, and a protocol template, and the like. The worklists storage repository 1408 may further include a tasks library 1412 containing user generated and user editable tasks such that the tasks are editable using predefined control options which are custom defined for each different type of worklist template. For example, the control options for a questionnaire template may be different from control options of the care plan template. The tasks are configured to be imported in a select worklist template from among the worklist templates to generate the computer executable worklist such that the computer executable worklist for a specific type may include user specific or customized tasks as retrieved from the templates saved in the tasks library 1412. While the templates of the worklists and the tasks may be predefined but the fact that these are user editable and customizable allows these to be specified for each specific device such as the first device 1502 or the second device 1504 or the third device 1506 to execute the tasks within the interaction zone 108.

The section A further includes the memory circuit 1406 coupled with the processing circuit 1402 and storing the plurality of application programming interfaces (APIs) 1404 providing the stack of API layers. The API layers may include a system API 1404a layer to allow communication with customer applications 1516. In some cases, the customer applications such as 1518 may have capabilities to call the system APIs 1404a directly while in some cases, the customer applications such as 1520 may not have system API calling capabilities as shown in FIG. 15. The customer applications 1516 may reside at the first device 1502, the second device 1504, and the third device 1506, in an embodiment. In an embodiment, the customer applications 1516 may reside at distinct locations but not at the first device 1502, the second device 1504, and the third device 1506 such as shown in FIG. 16.

The API layers may further include a supplementary modular, reusable and variably configurable independent API layer 1404b which can be stacked with the API layer stack within the ecosystem 1300 as a modular component to provide services such as secure authentication, data transfer, and data handling applications configured for interaction zone parameters signifying the triggering event comprising the spatial presence and weather-controlled event. The API layers may further include a business process modeling layer 1404d that unifies the worklists storage repository 1408 with the processing circuit 1402 to flexibly adapt to variations in the worklists storage repository 1408. The API layers may further include a data abstraction layer 1404c for enabling communication between the processing circuit 1402 and various data stores.

The ecosystem 1300 may further include a file-based interaction system 1414 including a first component communicatively and operatively connected with the processing circuit 1402 and a second component communicatively and operatively coupled with the first device 1502, the second device 1504, and the third device 1506. The second component may include an installable agent to cause the customer applications without API capability to interact with the system APIs 1404a indirectly through the first component and the second component, to collect information from the first device 1502, the second device 1504, and the third device 1506, and to interact with the worklists storage repository 1408.

The component B of the ecosystem 1300 includes a device operating region configured within or outside the interaction zone 108. However, it must be appreciated, that execution of a worklist task occurs at the future time occurrence when a triggering event is sensed. The device operating region includes the customer's applications without API capability 1520, the customer's applications with API capability 1518, a plurality of execution servers including the first execution server 1508, the second execution server 1510, and the third execution server 1512, a plurality of devices including the first device 1502, the second device 1504, and the third device 1506. The customer's applications (also referred to as device applications) with API capability 1518 can interact with the system APIs 1404a directly to allow execution of the computer executable worklist and the tasks contained therein. The customer's applications without API capability 1520 interact with the system APIs 1404a through the file-based interaction system 1414 to allow execution of the computer executable worklist and the tasks contained therein. The device operating region may further include sensors such as weather sensors 1522 and location sensors 1524.

The component C may include an electronic medical transactional system 1602 including or coupled to an electronic medical records database 1604. The electronic medical transactional system 1602 may be communicatively connected with the processing circuit 1402 and may store computer executable patient data files retrieved from disparate data sources. Each of the computer executable patient data files is associated with a first identification code that is indicative of a patient's identity, a second identification code that is indicative of a practitioner associated with the patient, a third identification code that is indicative of a set of tasks recommended for performance, in association with the patient, by the practitioner at the future time occurrence. The electronic medical transactional system 1602 collects real time and non-real time data from the disparate data sources. The real time data may be captured from such as electronic health records, browser applications and the like sources. The non-real time data may be captured from sources such as health information exchange sources, bio-informatics data sources, clinical data sources, pharmacy data sources and the like. The electronic medical transactional system 1602 may be configured to analyze the collected data, harmonize the data and perform a variety of processing and post processing activities before the processed data is served to the processing circuit 1402. Based on the data received by the processing circuit 1402, the processing circuit 1402 may design the computer executable worklist using the worklist templates and tasks templates so that the computer executable work list when executed at the future time occurrence causes particular steps to be performed as recommended through the electronic medical transactional system 1602. The electronic medical transactional system 1602 may include a memory device that stores transactional applications. The transactional applications can call the system APIs 1404a so as to integrate transactional elements with the processing circuit 1402. This allows the processing circuit 1402 to display on a display unit various analytical and processing information related to the data obtained from the disparate sources by the electronic medical transactional system 1602. The processing circuit 1402 thereon can take an action to generate the computer executable worklist for execution at the future time occurrence based on occurrence of the triggering event in the interaction zone 108. The communication between the electronic medical transactional system 1602 and the processing circuit 1402 is enabled through an installable agent device configured to be installed at the electronic medical transactional system 1602 in an embodiment. In another embodiment, the communication between the electronic medical transactional system 1602 and the processing circuit 1402 is enabled through browser extensions without using the installable agent device.

The component C may further include other external sources of work lists 1606 from where the work list templates may be imported by the processing circuit 1402 to schedule tasks for execution by the devices across various distributed systems. Various components in the component C may communicate with the processing circuit 1402 and the work lists storage repository 1408 from externally through applications with API capabilities 1518 and applications without capabilities 1520, external web applications 1608, and external mobile applications 1610. The applications with API capability 1518 can directly call the system APIs 1404a while the applications without API capabilities 1520 can interact with the file-based interaction system 1414 to call the system APIs 1404a.

In an embodiment, the ecosystem 1300 may provide a collaborative computer-implemented method for protocol documentation, automation, and compliance designed for a plurality of safety critical medical devices associated with patients through the worklists management system 400. The plurality of devices may be safety critical devices which may be associated with patients and may be used to collect and generate patient data. In an example, a protocol may be defined to be used as a shared baseline across the plurality of medical devices such that different tasks from the computer-executable worklist are performed and executed upon occurrence of the trigger event at the future time occurrence in view of guidelines maintained within the defined protocol. The protocol may be shared by the plurality of medical devices. The protocol may be used to manage definition, documentation, tracking, and analysis of the computer-executable tasks and procedures when the protocol (such as in the form of patient care plans etc as discussed earlier) is distributed across people, organizations, or systems or the plurality of medical devices. The protocol provides an enterprise-grade, integration-friendly solution which ensures that all processes, procedures, compliance requirements associated with well-defined protocols in an organization have been done in an intended sequence by required personnel or devices within a specified time period within the interaction zone. This allows the processes to be scalable, repeatable and provable.

In an example, the protocol may be defined for a specific patient as a patient treatment protocol indicative of the shared baseline across the plurality of medical devices associated with the patient. The protocol may be defined using an input from the electronic medical transactional system 1602. The list of computer executable tasks contained within the computer executable worklist may be received for automated execution in a defined protocol sequence by the plurality of execution servers 1508, 1510, and 1512 within the interaction zone. In an embodiment, authorized practitioners or devices (1502, 1504, and 1506) associated with them may be allowed to make modifications to the shared baseline protocol to adopt the shared baseline protocol for other patients with customized patient-centric variations. A report may be generated based on execution of the shared baseline protocol to identify tasks execution variations. The worklists management system 400 may be adopted to learn from the report to eliminate the variations over time arising from usage by different medical devices or different practitioners associated with the same patient while still maintaining flexibility to modify the shared baseline for different patients.

Further exemplary benefits of the work lists management system 400 and the ecosystem 1300 described above are provided hereafter without limitations.

Regulated Industries such as Healthcare, Life Sciences/BioTech and Medical Devices may be required to be process driven for various reasons such as patient safety and the like. Clinical enterprises may be challenged with defining processes (also called tasks, workflows, etc.) that are scalable, repeatable, and provable. Patient care plans may need to show evidence that required steps have been executed across multiple distributed systems such as Electronic Health Records (EHRs), lab equipment, digital pathology, imaging devices, or even manual procedures. Clinical organizations may use the system 400 to meet next generation demands of shared medical service organizations and other types of organizations. Current workflow and compliance tools are generally designed for single-organization use but the system 400 may be configured to automate protocol execution across clinical and other types of organizations.

The system 400 may allow complex care plans to be created and coordinated across complex distributed organizations that may be tied and coordinated at the patient level through a platform using Internet-savvy Application Programming Interfaces (APIs). The system 400 may provide regulated industries with an enterprise-grade, integration-friendly solution that ensures that all processes, procedures, compliance requirements associated with well-defined protocols in an organization have been done in an intended sequence by required personnel within a specified time period. The system 400 may ensure not only automation of protocols but proof of compliance of those protocols.

The system 400 may allow patient care plans, medical device connectivity, lab coordination, and similar complex tasks to be executed systematically with the help of easy to use work lists that may be defined without programmers or engineers. The work lists, which may be designed to be created by clinical personnel, may also be used as patient survey questionnaires, clinical process verifiers, medical care plans, regulatory mandate checkers and the like. The work lists may be versatile as they may allow for comments to be added, notifications to be sent, screenshots and attachments to be added, and tasks to be generated and assigned to staff members across multiple organizational boundaries.

The system 400 may provide a simple, yet fool proof method of ensuring that the work lists are run and completed at planned times by providing an option for scheduling the work lists and sending out notifications, to both clinical staff and patients, and reminding users to run them at defined time. Instead of static protocol documents, the system 400 may allow dynamic protocol execution and automation. Automatic notifications may go out and next run automatically enforces compliance when a care plan step changes.

The system 400 may provide patients with chronic conditions an ability to manage their health from the comfort of their home using next generation monitoring and wearable systems. The patients may use any kind of care plan that they would want to subscribe to such as losing weight, stopping smoking, managing their diet, handling exercise plans etc. The care plan may be as simple as reading an instruction from a doctor and simply following it through a mobile device. Clinicians and patients may be total synchronized with their care plans. The work lists may also act as questionnaires helping doctors collect information from patients before administering their care plan. This information may help doctors determine the best method of treatment based on the patient's lifestyle, behavior and other conditions.

The system 400 may track detailed statistics on care plans, work lists, and protocol automation so that Six Sigma or other Lean-style process engineering techniques may be used to improve and optimize clinical operations by performing "big data" analytics. The system 400 may allow analysts to understand whether complex, multi-organizational distributed processes are safely being executed and, based on real-time data, optimize for cost savings, patient satisfaction, patient safety, or a myriad of other factors.

The care plans, work lists, protocols, processes, and procedures may be created to be packaged in modules. This may allow, for example, small hospitals to use procedures created and branded by clinics. Researchers may cite use of regimented care plans in their clinical trials or other documentation. The system 400 may help prevent overuse of tests and procedures in a medical setup and may ensure that hospitals follow well defined guidelines in order to administer care for patients. This may save patients from doing a lot of unwanted tests and going through procedures which may not be required in the first place.

A lot of care needs to be taken while writing prescriptions and administering them. Potential drug interactions and correct dosages may also be ensured so that a patient receives right care. The system 400 may allow this by ensuring that hospital staff writing and administering prescriptions follow carefully laid down guidelines while writing or administering them. The system 400 may also help pharmacists with dispensing medicines with the help of guidelines or rules ensuring that right drugs are dispensed to right patients.

Generally, most healthcare institutions have routine tasks that may be simple or complex, that are repeatedly done either everyday as part of their routine clinical workflow tasks, or as part of specific medical procedures, blood tests, scans, etc. The system 400 may capture these routine tasks into work lists that may easily be run by anyone. These kinds of easy to do worklists make it easy for clinical personnel to get their jobs done faster and correctly with little or no chances of error thereby increasing their productivity.

The system 400 may ensure implementation of simple and complex tasks which are routine to help them manage patients health. Before a patient visits a doctor, he may have to run through a series of steps that are part of his routine visit. For example, he may need to do a blood test, check his blood pressure, get a scan done etc. Some of these tasks may need to done in a particular order and some of these may need to be done after reading an instruction. These kinds of tasks may be difficult for patients to remember and get them done especially if they are aged. The system 400 may help patients by informing them of an upcoming doctor's visit and letting them know what tests are due and taking them through these tests one step at a time. Once a test is done, they can mark them as done. Their doctors or caregivers may also get a notification that a particular patient has done all the tests that they had asked them to do.

In an example, the system 400 may be networked with WIFI enabled light emitting diodes (LEDs). The LEDs may be designed and defined to operate within the interaction zone. The LEDs may include sensors that may monitor presence, entry or exit of a person and transmit signals to the processing circuit 110 or the work lists management systems 400. The LEDs may monitor movements and manage work lists accordingly and/or initiate triggering events for performance of tasks. The LEDs may be controlled through a mobile phone, smart phones, or any other remote control device. In an example, when a new file is uploaded in a folder or at a server, the processing circuit 110 may send a notification to a user or a group of participants to have the user or the group of participants run a set of tasks from a work list assigned to them.

Healthcare providers visit for example elderly patients for routine checkup, glucose monitoring, blood analysis blood pressure check etc. If there is something that a healthcare provider need from a patient but don't want it done all the time or make a special trip for it, the embodiments herein may let the healthcare provider setup a tasks list or work list and then establish a rule that next time based on some trigger action (e.g. entering the facility or going of a patient to home, or when patient arrives and checks in the hospital) or next time when this event happens at specific conditions, drive these actions. These actions may for example ask patient a question and then fill a form. The list of tasks may be completely arbitrary.

In an embodiment, the system 400 may provide multi-discipline, multi-stakeholder, multi-institution, executable specifications for distributed workflows based on the interaction zone and time. Multi-discipline may represent that doctors, nurses, engineers, maintenance works, and the like from a variety of disciplines may create and manage their worklists in an executable (machine readable) manner with the use of a special purpose processor. Multi-stakeholder may represent that various tasks in the executable worklists can be run on behalf of a variety of stakeholders such as patients, their caregivers, and others that may not be associated within a healthcare ecosystem. Multi-institution may represent that a single executable worklist may have tasks that may be run across multiple legal organizations without limits. The worklists may be created and run by distributed disciplines for distributed stakeholders across distributed organizations. The executable worklists which are highly distributed may be timed to run for specific interaction results.

The embodiments herein provide a machine-readable executable specification that drives the worklist or protocol or process or procedure and then allows multiple institutions, stakeholders, and disciplines to interact with the executable worklist to allow enormous amounts of computer processing, quality checking, and numerous other computable activities to occur in real-time with the use of a special purpose processor. Therefore, workflows or protocols and the like defined by the worklist may be automated in accordance with the embodiments herein.

The embodiments herein may be embodied as a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon. Such non-transitory computer readable storage media can be any available media that can be accessed by a special purpose device, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose device to perform a certain function or group of functions. Computer-executable instructions also include program modules that are executed by computers in stand-alone or network environments. Generally, program modules include routines, programs, components, data structures, objects, and the functions inherent in the design of special-purpose devices, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

In an exemplary embodiment, the various modules described herein and illustrated in the figures are embodied as hardware-enabled modules and may be configured as a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that are configured with electronic circuits process computer logic instructions capable of providing digital and/or analog signals for performing various functions as described herein. The various functions can further be embodied and physically saved as any of data structures, data paths, data objects, data object models, object files, database components. For example, the data objects could be configured as a digital packet of structured data. The data structures could be configured as any of an array, tuple, map, union, variant, set, graph, tree, node, and an object, which be stored and retrieved by computer memory and may be managed by processors, compilers, and other computer hardware components. The data paths can be configured as part of a computer CPU that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be configured as physical locations in computer memory and can be a variable, a data structure, or a function. In the embodiments configured as relational databases (e.g., such Oracle® relational databases), the data objects can be configured as a table or column. Other configurations include specialized objects, distributed objects, object oriented programming objects, and semantic web objects, for example. The data object models can be configured as an application programming interface for creating HyperText Markup Language (HTML) and Extensible Markup Language (XML) electronic documents. The models can be further configured as any of a tree, graph, container, list, map, queue, set, stack, and variations thereof. The data object files are created by compilers and assemblers and contain generated binary code and data for a source file. The database components can include any of tables, indexes, views, stored procedures, and triggers.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor, and may be configured, for example, as a kiosk.

The embodiments herein can include both hardware and software elements. The embodiments that are implemented in software include but are not limited to, firmware, resident software, microcode, etc. Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk.

Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments herein is depicted in FIG. 17, with reference to FIGS. 1A through 16. This schematic drawing illustrates a hardware configuration of an information handling/computer system 1700 in accordance with the embodiments herein. The system 1700 comprises at least one processing device 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system 1300 can read the inventive instructions on the program storage devices and follow these instructions to execute the methodology of the embodiments herein. The system 1300 further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example. Further, a transceiver 26, a signal comparator 27, and a signal converter 28 may be connected with the bus 12 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A computer-implemented method for scheduling, tracking, and executing performance of a set of tasks, said method comprising:
   defining, by a special purpose processor in a repository, a time series;
   associating, by said special purpose processor in said repository, a current time occurrence on said time series;
   associating a future time occurrence, by said special purpose processor in a repository, on said time series, wherein said future time occurrence is defined as a succeeding time occurrence on said time series in relation to said current time occurrence;
   creating a tasks list including said set of tasks by a processing circuit, wherein said tasks list includes an actionable questionnaire, a test plan, a process verifier, a runbook, a careplan, a regulatory mandate that each are editable and executable at said future time occurrence;
   defining an interaction zone rule in association with said time series, wherein said step of defining said interaction zone rule includes defining a plurality of triggering events, by said special purpose processor, to initiate said set of tasks;
   associating said interaction zone rule with one or more participants in said repository;
   scheduling a task from said set of tasks at said future time occurrence relative to said current time occurrence based on occurrence of a triggering event in view of said interaction zone rule;
   receiving an output from an event monitor at a control server, said output indicative of said triggering event at said future time occurrence, wherein the event monitor comprises light emitting diodes to detect said triggering event;
   determining credentials of a user based on a user identification card read by an authorization interface connected to the control server;
   notifying a remote device for performance of said scheduled task at said future time occurrence upon detection of said triggering event; said step of notifying comprises:
      generating an electric signal comprising data signifying said schedule task and instructions for performance of said scheduled task;
      transmitting said electric signal from said control server, communicatively connected with said special purpose processor, in a network comprising a plurality of communicatively linked data communication devices;
      converting said electric signal into a plurality of pixels; and
      displaying said plurality of pixels on a display unit of said remote device to launch an activation message that includes an instruction to perform said scheduled task at said future time occurrence upon occurrence of said triggering event in accordance with said interaction zone rule;
   receiving a message by said control server from said remote device to update said set of tasks list and said time series dynamically based on a performance status of said scheduled task; and
   replacing said future time occurrence with a new current time occurrence in said repository and defining a new future time occurrence on said time series based on said performance status of said scheduled task and an input from said remote device that is indicative of health of a patient.

2. The method of claim 1, wherein said interaction zone rule is applied in association with an interaction zone defined by physical coordinates of a geographical location such that said triggering event is indicative of an entry of said remote device within said geographical location bounded by said physical coordinates at said future time occurrence.

3. The method of claim 2, further comprising detecting spatial presence of said remote device within said interaction zone with the use of a location sensor physically located within said interaction zone or associated with said remote device and capable of detecting transition of said remote device from outside to within said interaction zone.

4. The method of claim 1, wherein said interaction zone rule is applied in association with an interaction zone defined by physical coordinates of a geographical location such that said triggering event is indicative of a weather controlled event occurrence within said geographical location bounded by said physical coordinates at said future time occurrence.

5. The method of claim 4, further comprising monitoring weather parameters or said weather-controlled triggering event with the use of a weather sensor physically located within said interaction zone or associated with said remote device and capable of sending detected signals indicative of said weather-controlled triggering event to said control server.

6. The method of claim 5, wherein said weather-controlled triggering event comprises rain, humidity, and temperature, such that said weather sensor comprises a rain sensor, a temperature sensor, and a humidity sensor, wherein said weather sensor is capable of sending signals to said control server indicative of occurrence of said weather-controlled triggering event only at said future time occurrence.

7. A computer-controlled system for scheduling, tracking, and executing performance of a set of tasks, said system comprising:
  a control server configured to communicatively connect with a remote device through a network for allowing exchange of computer executable patient data between said control server and said remote device;
  an authorization interface connected to the control server to implement an authentication policy to determine credentials of a user based on a user identification card read by the authorization interface;
  a special purpose processor included within or communicatively connected with said control server to:
    define a time series in a repository;
    associate a current time occurrence on said time series in a repository;
    associate a future time occurrence on said time series in a repository, wherein said future time occurrence is defined as a succeeding time occurrence on said time series in relation to said current time occurrence;
    create a tasks list including said set of tasks in a repository, wherein said tasks list includes an actionable questionnaire, a test plan, a process verifier, a runbook, a careplan, a regulatory mandate that each are editable and executable at said future time occurrence;
    define an interaction zone rule in association with said time series, wherein said step of defining said interaction zone rule includes defining a plurality of triggering events, by said special purpose processor, to initiate said set of tasks;
    associate said interaction zone rule with one or more participants in a repository;
    schedule a task from said set of tasks at said future time occurrence relative to said current time occurrence based on occurrence of a triggering event in view of said interaction zone rule;
    receive an input indicative of said triggering event at said future time occurrence;
    notify said remote device for performance of said scheduled task at said future time occurrence upon detection of said triggering event; said step of notifying comprises:
      generating an electric signal comprising data signifying said schedule task and instructions for performance of said scheduled task;
      transmitting said electric signal in a network comprising a plurality of communicatively linked data communication devices;
      converting said electric signal into a plurality of pixels; and
      displaying said plurality of pixels on a display unit of said remote device to launch an activation message that includes an instruction to perform said scheduled task at said future time occurrence upon occurrence of said triggering event in accordance with said interaction zone rule;
    receive a message from said remote device to update said set of tasks list and said time series dynamically based on performance status of said task; and
    replace said future time occurrence with a new current time occurrence and define a new future time occurrence on said time series in a repository based on said performance status of said scheduled task and an input from said remote device that is indicative of health of a patient; and
  an event monitor comprising a location sensor and a weather sensor communicatively connected with said control server for detecting spatial presence and a weather controlled event respectively upon occurrence of said triggering event.

8. The system of claim 7, further comprising an electronic medical records database communicatively connected with said control server, said electronic medical records database storing computer executable patient data files, wherein each of said computer executable patient data files is associated with a first identification code that is indicative of a patient's identity, a second identification code that is indicative of a practitioner associated with said patient, a third identification code that is indicative of a set of tasks recommended for performance, in association with said patient, by said practitioner at said current time occurrence.

9. The system of claim 8, wherein said current time occurrence is associated with a last visit of said practitioner in said interaction zone for said patient.

10. The system of claim 8, wherein said future time occurrence is associated with occurrence of said triggering event such that said future time occurrence is set to occur after a predefined number of said triggering event has occurred within said interaction zone, wherein said predefined number is dynamically adjusted by said special purpose processor based on an input received from said remote device including a computer executable file signifying health status of said patient and a recommendation note by said practitioner.

11. The system of claim 8, wherein said interaction zone is defined to exhibit preset capabilities within a defined spatial coordinate of a geographical location to allow information exchange between said control server and said remote device within said interaction zone, wherein said performance of said set of tasks is limited within said spatial coordinates of said interaction zone in view of said interaction zone rule.

12. A computer-controlled worklists management system for creating, scheduling and facilitating execution of a computer executable worklist across a plurality of distributed execution servers, said system comprising:
a processing circuit to:
generate said computer executable worklist, said computer executable worklist comprising a plurality of tasks scheduled to be executed at a future time occurrence on a time series based on occurrence of a triggering event in view of an interaction zone rule indicative of a spatial presence and a weather controlled event within an interaction zone, wherein said plurality of tasks include at least a first task executable by a first device controlled by a first execution server, a second task executable by a second device controlled by a second execution server, a third task executable by a third device controlled by a third execution server, wherein said first execution server, said second execution server, and said third execution server are located remotely in a distributed environment;
an authorization interface integrated with the processing circuit to implement an authentication policy to determine credentials of a user based on a user identification card read by the authorization interface;
a worklists storage repository comprising:
a worklists library containing predefined and user editable worklist templates, said worklists library including a survey template, a check list template, a care plan template, a questionnaire template, and a protocol template;
a task library containing user generated and user editable tasks such that said tasks are editable using predefined control options, wherein said tasks are configured to be imported in a select worklist template from among said worklist templates to generate said computer executable worklist;
a memory circuit coupled to said processing circuit and storing a plurality of internet-based application programming interfaces (APIs) providing a stack of API layers comprising:
a system API layer to allow communication with 1) customer applications with API capability directly 2) customer applications without API capability indirectly, wherein said customer applications reside at said first device, said second device, and said third device;
a supplementary modular, reusable and variably configurable independent API layer for secure authentication, data transfer, and data handling applications configured for interaction zone parameters signifying said triggering event comprising said spatial presence and weather-controlled event;
a business process modeling layer that unifies said worklists storage repository with said processing circuit; and
a data abstraction layer for enabling communication between said processing circuit and data stores; and
a file-based interaction device including a first component communicatively and operatively connected with said processing circuit and a second component communicatively and operatively coupled with said first device, said second device, and said third device, wherein said second component comprises an installable agent to:
cause said customer applications without API capability to interact with said system APIs indirectly through said first component and said second component;
collect information from said first device, said second device, and said third device; and
interact with said workflow storage engine.

13. The system of claim 12, wherein said interaction zone rule is applied in association with said interaction zone defined by physical coordinates of a geographical location such that said triggering event is indicative of an entry of said first device, said second device, and said third device within said geographical location bounded by said physical coordinates at said future time occurrence.

14. The system of claim 12, wherein said spatial presence of said first device, said second device, and said third device within said interaction zone is detected with the use of a location sensor physically located within said interaction zone or associated with said first device, said second device, and said third device and capable of detecting transition of said first device, said second device, and said third device from outside to within said interaction zone.

15. The system of claim 12, further comprising a WIFI-enabled Light Emitting Diode within said interaction zone that contains said location sensor and said weather sensor and is configured to operate within said interaction zone to monitor presence, entry or exit and transmits signals to said processing circuit.

16. The system of claim 12, wherein said interaction zone rule is applied in association with said interaction zone defined by physical coordinates of a geographical location such that said triggering event is indicative of a weather controlled event occurrence within said geographical location bounded by said physical coordinates at said future time occurrence.

17. The system of claim 16, wherein a weather parameter or said weather-controlled triggering event is monitored with the use of a weather sensor physically located within said interaction zone or associated with said first device, said second device, and said third device and capable of sending detected signals indicative of said weather-controlled triggering event to said processing circuit, wherein said weather-controlled triggering event comprises rain, humidity, and temperature, such that said weather sensor comprises a rain sensor, a temperature sensor, and a humidity sensor, and wherein said weather sensor is capable of sending signals to said processing circuit indicative of occurrence of said weather-controlled triggering event only at said future time occurrence.

18. The system of claim 12, further comprising an electronic medical transactional system including an electronic medical records database communicatively connected with or included within said electronic medical transactional system, said electronic medical records database storing computer executable patient data files, wherein each of said computer executable patient data files is associated with a first identification code that is indicative of a patient's identity, a second identification code that is indicative of a practitioner associated with said patient, a third identification code that is indicative of a set of tasks recommended for performance, in association with said patient, by said practitioner at said future time occurrence.

19. The system of claim 12, further comprising external sources of work lists that supply said user editable worklist templates to said processing circuit to schedule said plurality of tasks for execution by said plurality of execution servers across said distributed devices.

20. A collaborative computer-implemented method for protocol documentation, automation, and compliance designed for a distributed safety critical plurality of devices, said method comprising:

defining a patient treatment protocol, indicative of a shared baseline, for a first patient using an input from an electronic medical transactional system, wherein said electronic medical transactional system comprises an electronic medical records database communicatively connected with or included within said electronic medical transactional system, said electronic medical records database storing computer executable patient data files, wherein each of said computer executable patient data files is associated with a first identification code that is indicative of a patient's identity, a second identification code that is indicative of a practitioner associated with said patient;

receiving a list of computer executable tasks contained within a computer executable worklist for automated execution in a defined protocol sequence by a plurality of execution servers within an interaction zone, wherein said computer executable worklist is created by a worklist management system using protocol-compliant user customizable options, said worklist management system operatively connected with a control server located remote from said interaction zone;

determining credentials of a user based on a user identification card read by an authorization interface connected to the control server;

defining, by a special purpose processor in a repository, a time series;

associating, by said special purpose processor in said repository, a current time occurrence on said time series;

associating a future time occurrence, by said special purpose processor in a repository, on said time series, wherein said future time occurrence is defined as a succeeding time occurrence on said time series in relation to said current time occurrence;

defining an interaction zone rule in association with said time series, wherein said step of defining said interaction zone rule includes defining a plurality of triggering events, by said special purpose processor, to initiate said set of tasks in accordance with said shared baseline protocol across said plurality of devices;

receiving an output from an event monitor at said control server, said output indicative of said triggering event at said future time occurrence in association with a device from said plurality of devices, wherein the event monitor comprises light emitting diodes to detect said triggering event;

notifying said device for performance of a scheduled task at said future time occurrence upon detection of said triggering event;

allowing modifications by an authorized practitioner to said shared baseline protocol to adopt said shared baseline protocol for a second patient with customized patient-centric variations; and generating a report based on execution of said shared baseline protocol in association with plurality of devices to identify tasks execution variations.

\* \* \* \* \*